United States Patent [19]

Dörreich et al.

[11] Patent Number: 5,538,884
[45] Date of Patent: Jul. 23, 1996

[54] RHAMNOGALACTURONASE, CORRESPONDING DNA SEQUENCE, RHAMNOGALACTURONASE CONTAINING ENZYME PREPARATION AND USE OF THE ENZYME PREPARATION

[75] Inventors: Kurt Dörreich, Grenzach-Wyhlen, Germany; Henrik Dalbøge, Virum, Denmark; Jan M. Mikkelsen, Gentofte, Denmark; Flemming M. Christensen, Rungsted Kyst, Denmark; Torben Halkier, Frederiksberg, Denmark

[73] Assignee: Novo Nordisk A/S, Bagsvaerd, Denmark

[21] Appl. No.: 140,188

[22] PCT Filed: May 1, 1992

[86] PCT No.: PCT/DK92/00143

§ 371 Date: Dec. 15, 1993

§ 102(e) Date: Dec. 15, 1993

[87] PCT Pub. No.: WO92/19728

PCT Pub. Date: Nov. 12, 1992

[30]     Foreign Application Priority Data

May 2, 1991  [EP]  European Pat. Off. .............. 91610039

[51] Int. Cl.$^6$ ............................ C12N 9/24; C12N 9/40; C07H 19/00; C07H 21/00
[52] U.S. Cl. .......................... 435/200; 435/208; 435/209; 536/22.1; 536/23.1; 536/23.2; 536/23.7; 536/23.74
[58] Field of Search ................................ 435/200, 208, 435/209; 536/22.1, 23.1, 23.2, 23.7, 23.74

[56]          References Cited

U.S. PATENT DOCUMENTS 4,478,939  10/1984  Alder-Nissen ................. 435/200
4,478,940  10/1984  Alder-Nissen et al. ........ 435/209

FOREIGN PATENT DOCUMENTS 0383593  9/1990  European Pat. Off. .
2115820  9/1983  United Kingdom .

OTHER PUBLICATIONS

H. A. Schols, Carbohydrate Research, vol. 206, pp. 105–115, 1990.
I. J. Colquhoum et al., Carbohydrate Research, vol. 206, pp. 131–144, 1990.
J. M. Brillouet, Rev. Fr. Oenol., vol. 122, pp. 43–54, 1990 (no translation).

*Primary Examiner*—Robert A. Wax
*Assistant Examiner*—Hyosuk Kim
*Attorney, Agent, or Firm*—Steve T. Zelson, Esq.; Elias J. Lambiris, Esq.

[57]          ABSTRACT

The present invention relates to rhamnogalacturonases derived from a strain of *Aspergillus japonicus* which (a) has a pH-optimum between 6.5 and 7.0; (b) retains at least 80% of the maximal activity throughout the pH range of 5.5–12; (c) has a temperature optimum of about 40° C.; and (d) retains at least 80% of the maximal activity throughout the temperature range of 20°–60° C. The present invention relates to rhamnogalacturonases derived from a stain of *Aspergillus aculeatus* which (a) has a pH-optimum of about 5.0; (b) retains at least 80% of the maximal activity throughout the pH range of 3–6.5; (c) has a temperature optimum of about 40° C.; and (d) retains at least 80% of the maximal activity throughout the temperature range of 5°–50° C.

16 Claims, 24 Drawing Sheets

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Aspergillus aculeatus
        ( B ) STRAIN: CBS 101.43

( x i ) SEQUENCE DESCRIPTION: SEQ ID NO:1:

```
Gly Ala Val Gln Gly Phe Gly Tyr Val Tyr His Ala Glu Gly Thr Tyr
 1               5                  10                  15

Gly Ala Arg
```

( 2 ) INFORMATION FOR SEQ ID NO:2:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Aspergillus aculeatus
        ( B ) STRAIN: CBS 101.43

( x i ) SEQUENCE DESCRIPTION: SEQ ID NO:2:

```
Ser Xaa Asn Ile Leu Ser Tyr Gly Ala Val Ala Asp Xaa Ser Thr Asp
 1               5                  10                  15
```

Val Gly Pro Ala Ile Thr Ser Ala Xaa Ala Ala Arg Lys
            20                      25

(2) INFORMATION FOR SEQ ID NO:3:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: Aspergillus aculeatus
        (B) STRAIN: CBS 101.43

(xi) SEQUENCE DESCRIPTION: SEQ ID NO:3:

Ser Arg Asn Ile
1

(2) INFORMATION FOR SEQ ID NO:4:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: Aspergillus aculeatus
        (B) STRAIN: CBS 101.43

(xi) SEQUENCE DESCRIPTION: SEQ ID NO:4:

Ser Ala Tyr Gly Ser Gly Tyr Xaa Leu Lys
1               5                   10

(2) INFORMATION FOR SEQ ID NO:5:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: Aspergillus aculeatus
        (B) STRAIN: CBS 101.43

(xi) SEQUENCE DESCRIPTION: SEQ ID NO:5:

Thr Leu Glu Asp Ile Ala Ile
1               5

(2) INFORMATION FOR SEQ ID NO:6:

(i) SEQUENCE CHARACTERISTICS:

(A) LENGTH: 16 amino acids
(B) TYPE: amino acid
(C) STRANDEDNESS: single
(D) TOPOLOGY: linear (ii) MOLECULE TYPE: protein (iii) HYPOTHETICAL: NO (iv) ANTI-SENSE: NO (vi) ORIGINAL SOURCE:
(A) ORGANISM: Aspergillus aculeatus
(B) STRAIN: CBS 101.43

(xi) SEQUENCE DESCRIPTION: SEQ ID NO:6:

Gly Leu Xaa Ala Xaa Ile Pro Ile Pro Xaa Ile Pro Pro Xaa Phe Phe
1               5                   10                  15

(2) INFORMATION FOR SEQ ID NO:7:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: protein (iii) HYPOTHETICAL: NO (iv) ANTI-SENSE: NO (vi) ORIGINAL SOURCE:
(A) ORGANISM: Aspergillus aculeatus
(B) STRAIN: CBS 101.43

(xi) SEQUENCE DESCRIPTION: SEQ ID NO:7:

Ser Leu Asp Ile Asp Gly Tyr
1               5

(2) INFORMATION FOR SEQ ID NO:8:

(i) SEQUENCE CHARACTERISTICS:
(A) LENGTH: 13 amino acids
(B) TYPE: amino acid
(C) STRANDEDNESS: single
(D) TOPOLOGY: linear (ii) MOLECULE TYPE: protein (iii) HYPOTHETICAL: NO (iv) ANTI-SENSE: NO (vi) ORIGINAL SOURCE:
(A) ORGANISM: Aspergillus aculeatus
(B) STRAIN: CBS 101.43

(xi) SEQUENCE DESCRIPTION: SEQ ID NO:8:

Ser Val His Asp Ile Ile Leu Val Asp Ala Pro Ala Phe
1               5                   10

(2) INFORMATION FOR SEQ ID NO:9:

(i) SEQUENCE CHARACTERISTICS:
(A) LENGTH: 5 amino acids
(B) TYPE: amino acid
(C) STRANDEDNESS: single
(D) TOPOLOGY: linear (ii) MOLECULE TYPE: protein (iii) HYPOTHETICAL: NO ( i v ) ANTI-SENSE: NO ( v i ) ORIGINAL SOURCE:
    ( A ) ORGANISM: Aspergillus aculeatus
    ( B ) STRAIN: CBS 101.43

( x i ) SEQUENCE DESCRIPTION: SEQ ID NO:9:

```
Ala  Ala  Asp  Leu  Ala
1                     5
```

( 2 ) INFORMATION FOR SEQ ID NO:10:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
    ( A ) ORGANISM: Aspergillus aculeatus
    ( B ) STRAIN: CBS 101.43

( x i ) SEQUENCE DESCRIPTION: SEQ ID NO:10:

```
Gly  Ser  Asn  Ile
1
```

( 2 ) INFORMATION FOR SEQ ID NO:11:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
    ( A ) ORGANISM: Aspergillus aculeatus
    ( B ) STRAIN: CBS 101.43

( x i ) SEQUENCE DESCRIPTION: SEQ ID NO:11:

```
Tyr  Pro  Gly  Leu  Thr  Pro  Tyr
1                     5
```

( 2 ) INFORMATION FOR SEQ ID NO:12:

( i ) SEQUENCE CHARACTERISTICS:
    ( A ) LENGTH: 14 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
    ( A ) ORGANISM: Aspergillus aculeatus
    ( B ) STRAIN: CBS 101.43

( x i ) SEQUENCE DESCRIPTION: SEQ ID NO:12:

```
    Asn  Val  Tyr  Thr  Trp  Ser  Ser  Asn  Gln  Met  Tyr  Met  Ile  Lys
    1              5                        10
```

( 2 ) INFORMATION FOR SEQ ID NO:13:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: A. japonicus
        ( B ) STRAIN: ATCC 20236

( x i ) SEQUENCE DESCRIPTION: SEQ ID NO:13:

```
    Ala  Phe  Gly  Ile  Thr  Thr  Ser  Ser  Ser  Ala  Tyr  Val  Ile  Asp  Thr  Asp
    1              5                        10                       15

Ala  Pro  Asn  Gln  Leu  Lys  Xaa  Thr  Val  Ser  Arg
                   20                  25
```

( 2 ) INFORMATION FOR SEQ ID NO:14:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Irpex lacteus
        ( B ) STRAIN: ATCC 20157

( x i ) SEQUENCE DESCRIPTION: SEQ ID NO:14:

```
    Asn  Val  Asn  Leu  Phe  Ile  Thr  Asp  Gly  Ala  Arg
    1              5                        10
```

( 2 ) INFORMATION FOR SEQ ID NO:15:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Irpex lacteus
        ( B ) STRAIN: atcc 20157

( x i ) SEQUENCE DESCRIPTION: SEQ ID NO:15:

```
    Ala  Pro  Asp  Gly  Pro  Ala
    1              5
```

RHAMNOGALACTURONASE, CORRESPONDING DNA SEQUENCE, RHAMNOGALACTURONASE CONTAINING ENZYME PREPARATION AND USE OF THE ENZYME PREPARATION

CROSS-REFERENCE TO RELATED APPLICATIONS

This application is a continuation of PCT/DK92/00143 filed May 1, 1992, which is incorporated herein by reference.

BACKGROUND OF THE INVENTION

1. Field of the Invention

The invention comprises a rhamnogalacturonase (in the following usually abbreviated RGase), a corresponding DNA sequence, an RGase containing enzyme preparation and a use of the enzyme preparation.

Thus, the invention relates to genetic engineering and provides partial amino acid sequences of an RGase. These partial amino acid sequences can be used for construction of DNA probes which can be used for screening a genomic library from organisms expressing such enzyme, or a cDNA library, thereby obtaining DNA sequences, which can be used either for an overproduction of RGase, if inserted in the microorganism species, from which the parent DNA molecule originated, or for production of RGase without accompanying closely related enzymes, if inserted in a host microorganism, which in its not-transformed condition does not produce any enzymes closely related to RGase.

2. Description of Related Art

Plant cell walls comprising rhamnogalacturonans are of complex nature. Many publications deal with the polysaccharides serving as building blocks, of which these cell walls consist, and their importance with respect to the growing, ripening and processing of fruits and vegetables. Especially pectins have been studied frequently, because they are among the most important components in this respect. Pectins are proposed to consist of highly carboxyl-methylated linear homogalacturonan regions which alternate with "hairy" (ramified) regions that comprise highly branched rhamnogalacturonans mainly. Whereas the linear homogalacturonan regions are very well known and characterized, the structure of the so-called hairy regions is still not fully characterized, and thus is the subject of many investigations. But besides the scientific interest it is very important to be able to degrade these hairy regions for technical reasons. The enzymatic liquefaction of plant material like e.g. fruits, vegetables, cereals, oil fruits and seeds by technical processes involves combinations of pectolytic, cellulolytic and proteolytic enzyme preparations. This enzymatic treatment solubilizes the hairy regions and other pectic fragments, which originate from the insoluble cell wall protopectin. On one hand the solubilization of these polysaccharides is wanted, e.g. for the production of cloudy liquids and soluble dietary fiber containing solutions. On the other hand these polysaccharides cause problems during the processing of the clear liquids, because they are resistant to complete degradation of most technical enzyme preparations. Only one enzyme preparation (from *Aspergillus aculeatus*) has so far been described, which can degrade the rhamnogalacturonan backbone of the hairy regions. Therefore, it is of great importance for scientific (studies of the structures of these complex polysaccharides) and technical (liquefaction of plant material) reasons to obtain more knowledge about enzymes that can degrade these hairy regions. Especially for the industries dealing with modifications of plant cell walls for e.g. human nutrition and for animal feed (e.g. liquefaction of fruits, vegetables, cereals, oil fruits and seeds), it is of great importance to provide a great variety of different RGases (in respect to mode of action, pH and temperature range) in order to be able to exploit the desirable actions of RGases under widely varying technical process conditions.

RGase is described in the poster "Rhamnogalacturonase; a novel enzyme degrading the highly branched rhamnogalacturonan regions in apple pectic substances" from Wageningen Agricultural University, Department of Food Science, Biotechnion, Bomenweg 2,6703 HD Wageningen, The Netherlands. From this poster is appears that a rhamnogalacturonase, the origin of which is not described, is well suited for degradation of the backbone of a modified "hairy region" (MHR) in plant cell walls. Also, it is described that this enzyme might play a role in the degradation of plant cell wall tissue, particularly in combination with other enzymes. However, it is not specified which other enzymes.

Also, the isolation and purification of RGase from *Aspergillus aculeatus* is described by Schois et al. in Carbohydrate Research 206 (1990) 105–115, "Rhamnogalacturonase: a novel enzyme, that degrades the hairy regions of pectins". From page 11, line 1 it appears that RGase has been purified to a high degree of purity as it moved as a single band in SDS-polyacrylamide gel electrophoresis.

Furthermore, in an article of Colquhoun in Carbohydrate Research 206 (1990) 131–144, "Identification by n.m.r. spectroscopy of oligosaccharides obtained by treatment of the hairy regions of apple pectin with rhamnogalacturonase" the composition of a mixture of oligosaccharides obtained by enzymatic degradation of the modified hairy (ramified) regions of apple pectin with a RGase is described.

The extraction of apple pectins by RGase is further described in the poster "Extraction of apple pectins by rhamnogalacturonase, a new pectolytic enzyme" by C.M.G.C. Renard et al., Laboratoire de Biochimie et Technologie des Glucides, INRA, Nantes (France).

To the best of applicant's knowledge, only a single species of RGase belongs to the prior art, and has been purified, i.e. the *A. aculeatus* RGase described by Schols et al., this RGase being the RGase appearing in all the previously indicated references. Also, this RGase has only been partly characterized and has not been characterized in regard to amino acid sequence, the corresponding RGase produced gene has not been cloned, and thus, the prior art RGase has not been available as a cheap, industrially useable product.

Thus, in consideration of what has been indicated previously, there is a great need for the provision of a variety of RGases with different properties corresponding to the conditions, under which rhamnogalacturonans have to be degraded industrially, e.g. different specificity, pH optimum and temperature optimum. Secondly, there is a need for cheap and pure RGases which can be used industrially in an economically sound manner.

Thus, the purpose of the invention is the provision of an RGase, which covers embodiments exhibiting varying characteristics corresponding to the different industrial conditions, under which rhamnogalacturonans have to be degraded, and of an RGase, which can be produced in better yield, and thus cheaper, than hitherto possible, and in higher purity. Also, it is the purpose of the invention to provide novel products, wherein the proportion of the RGase is either increased or decreased in relation to the proportion in the original product.

SUMMARY OF THE INVENTION

Accordingly the RGase according to the invention is characterized by the following amino acid sequences:

```
1               5               10              15           (SEQ ID NO: 1)
Gly—Ala—Val—Gln—Gly—Phe—Gly—Tyr—Val—Tyr—His—Ala—Glu—Gly—Thr

Tyr—Gly—Ala—Arg 1               5               10              15           (SEQID NO: 2)
Ser—Xaa—Asn—Ile—Leu—Ser—Tyr—Gly—Ala—Val—Ala—Asp—Xaa—Ser—Thr—

20              25
Asp—Val—Gly—Pro—Ala—Ile—Thr—Ser—Ala—Xaa—Ala—Ala—Arg—Lys 1                                                            (SEQ ID NO: 3)
Ser—Arg—Asn—Ile 1               5               10                           (SEQ ID NO: 4)
Ser—Ala—Tyr—Gly—Ser—Gly—Tyr—Xaa—Leu—Lys 1               5                                            (SEQ ID NO: 5)
Thr—Leu—Glu—Asp—Ile—Ala—Ile 1               5               10              15           (SEQ ID NO: 6)
Gly—Leu—Xaa—Ala—Xaa—Ile—Pro—Ile—Pro—Xaa—Ile—Pro—Pro—Xaa—Phe—

Phe 1               5                                            (SEQ ID NO: 7)
Ser—Leu—Asp—Ile—Asp—Gly—Tyr 1               5               10                           (SEQ ID NO: 8)
Ser—Val—His—Asp—Ile—Ile—Leu—Val—Asp—Ala—Pro—Ala—Phe 1               5                                            (SEQ ID NO: 9)
Ala—Ala—Asp—Leu—Ala—

1                                                            (SEQ ID NO: 10)
Gly—Ser—Asn—Ile 1               5                                            (SEQ ID NO: 11)
Tyr—Pro—Gly—Leu—Thr—Pro—Tyr 1               5               10                           (SEQID NO: 12)
Asn—Val—Tyr—Thr—Trp—Ser—Ser—Asn—Gln—Met—Tyr—Met—Ile—Lys 1               5               10              15           (SEQ ID NO: 13)
Ala—Phe—Gly—Ile—Thr—Thr—Ser—Ser—Ser—Ala—Tyr—Val—Ile—Asp—Thr—

20              25
Asp—Ala—Pro—Asn—Gln—Leu—Lys—Xaa—Thr—Val—Ser—Arg 1               5               10                           (SEQ ID NO: 14)
Asn—Val—Asn—Leu—Phe—Ile—Thr—Asp—Gly—Ala—Arg 1               5                                            (SEQ ID NO: 15)
Ala—Pro—Asp—Gly—Pro—Ala—
``` or a partial amino acid sequence, preferably an N-terminal amino acid sequence with a homology thereto of at least 70%, preferably at least 80%, more preferably at least 90%. To the best of applicants knowledge this class of RGases is a new class of RGases with an advantageously high ability to degrade rhmanogalacturonans under the varying conditions appearing in industry.

BRIEF DESCRIPTION OF THE DRAWINGS

The present invention is further illustrated by reference to the accompanying drawings, wherein.

DETAILED DESCRIPTION OF THE INVENTION

A preferred embodiment of the RGase according to the invention is characterized by the following partial amino acid sequences:

```
  1                 5                  10                 15           (SEQ ID NO: 1)
Gly—Ala—Val—Gln—Gly—Phe—Gly—Tyr—Val—Tyr—His—Ala—Glu—Gly—Thr

Tyr—Gly—Ala—Arg 1                 5                  10                 15           (SEQ ID NO: 2)
Ser—Xaa—Asn—Ile—Leu—Ser—Tyr—Gly—Ala—Val—Ala—Asp—Xaa—Ser—Thr—

20                 25
Asp—Val—Gly—Pro—Ala—Ile—Thr—Ser—Ala—Xaa—Ala—Ala—Arg—Lys 1                                                                    (SEQ ID NO: 3)
Ser—Arg—Asn—Ile 1                 5                  10                              (SEQ ID NO: 4)
Ser—Ala—Tyr—Gly—Ser—Gly—Tyr—Xaa—Leu—Lys 1                 5                                                  (SEQ ID NO: 5)
Thr—Leu—Glu—Asp—Ile—Ala—Ile 1                 5                  10                 15           (SEQ ID NO: 6)
Gly—Leu—Xaa—Ala—Xaa—Ile—Pro—Ile—Pro—Xaa—Ile—Pro—Pro—Xaa—Phe—

Phe 1                 5                                                  (SEQ ID NO: 7)
Ser—Leu—Asp—Ile—Asp—Gly—Tyr 1                 5                  10                              (SEQ ID NO: 8)
Ser—Val—His—Asp—Ile—Ile—Leu—Val—Asp—Ala—Pro—Ala—Phe 1                 5                                                  (SEQ ID NO: 9)
Ala—Ala—Asp—Leu—Ala—

1                                                                    (SEQ ID NO: 10)
Gly—Ser—Asn—Ile 1                 5                                                  (SEQ ID NO: 11)
Tyr—Pro—Gly—Leu—Thr—Pro—Tyr 1                 5                  10                              (SEQ ID NO: 12)
Asn—Val—Tyr—Thr—Trp—Ser—Ser—Asn—Gln—Met—Tyr—Met—Ile—Lys
```

Figure 16:
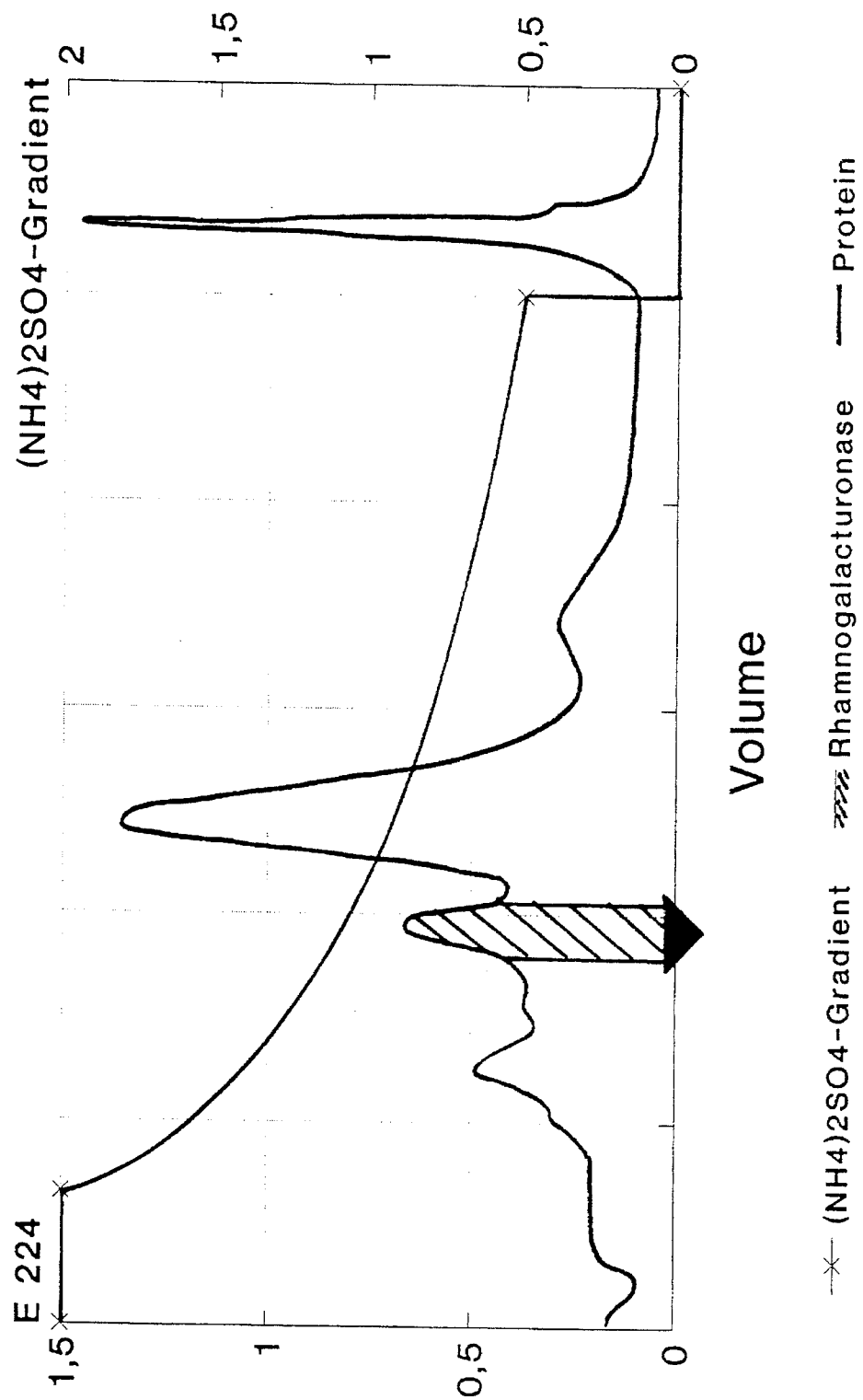

FIG. 16 shows a hydrophobic interaction chromatogram of the process for purifying an *Irpex lacteus* acteus rhamnogalacturonase.

Figure 17:
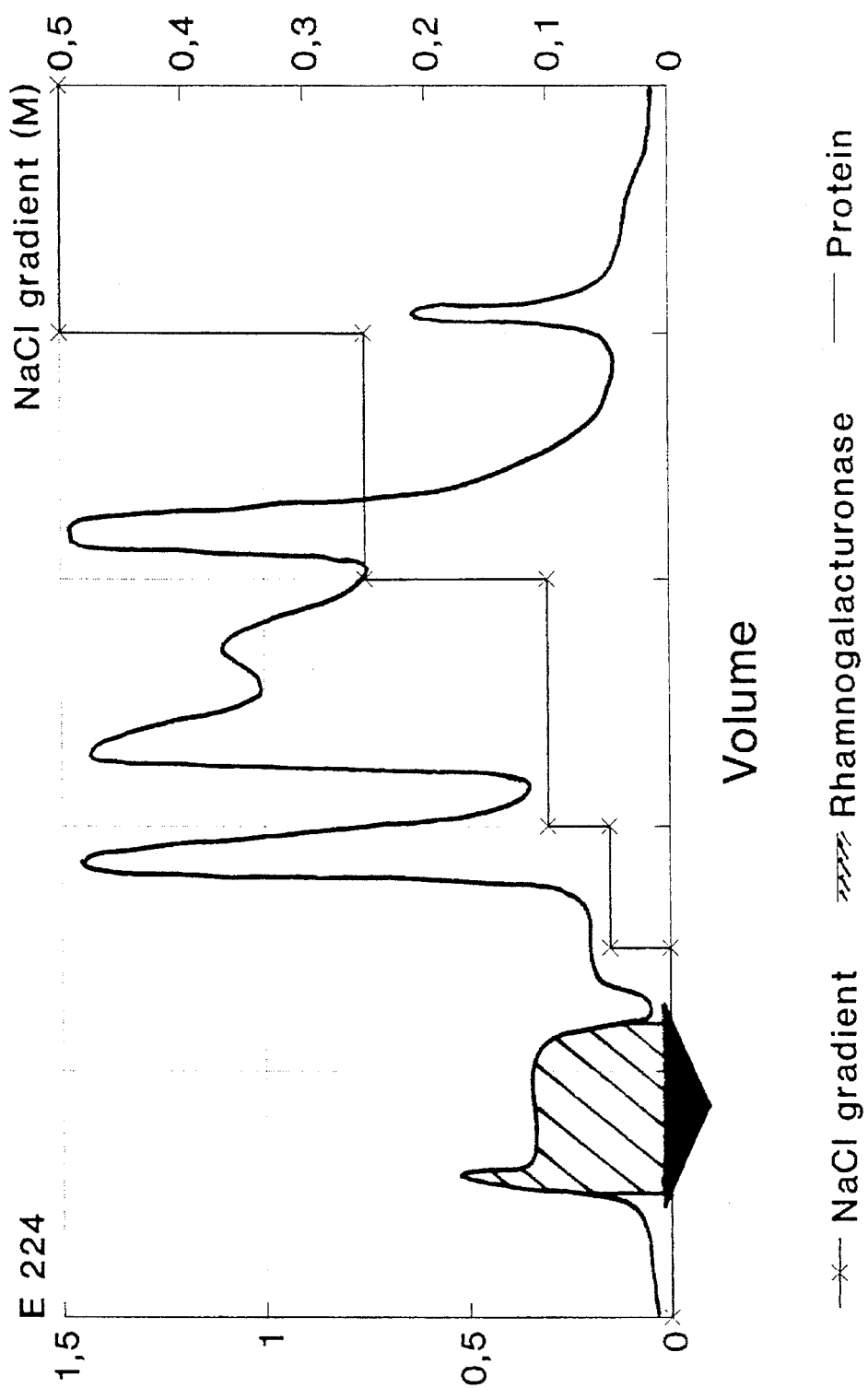

FIG. 17 shows an ion exchange chromatogram of the process for purifying an *Irpex lacteus* rhamnogalacturonase.

or a partial amino acid sequence, preferably an N-terminal amino acid sequence with a homology thereto of at least 70%, preferably at least 80%, more preferably at least 90%.

A preferred embodiment of the RGase according to the invention is characterized by the following partial amino acid sequence:

```
  1                 5                  10                 15           (SEQ ID NO: 13)
Ala—Phe—Gly—Ile—Thr—Thr—Ser—Ser—Ser—Ala—Tyr—Val—Ile—Asp—Thr—
```

—Asp—Ala—Pro—Asn—Gln—Leu—Lys—Xaa—Thr—Val—Ser—Arg

A preferred embodiment of the RGase according to the invention is characterized by the following partial amino acid sequences (SEQ ID NO: 14)

1       5       10
Asn—Val—Asn—Leu—Phe—Ile—Thr—Asp—Gly—Ala—Arg 1       5       SEQ ID NO: 15)
—Ala—Pro—Asp—Gly—Pro—Ala—

A preferred embodiment of the RGase according to the invention is characterized by being obtainable by means of *Aspergillus aculeatus*, CBS 101.43.

A preferred embodiment of the RGase according to the invention is characterized by being obtainable by means of *A. japonicus* ATCC 20236.

A preferred embodiment of the RGase according to the invention is characterized by being obtainable by means of *Irpex lacteus* ATCC 20157.

Also, the invention comprises a recombinant DNA sequence, which comprises a DNA sequence coding for a polypeptide having RGase activity, or a DNA sequence having substantial sequence homology to such RGase coding sequence, preferably a homology of at least 70%, more preferably at least 80%, and most preferably at least 90%.

A preferred embodiment of the recombinant DNA sequence according to the invention comprises a DNA sequence selected from a) the *A. aculeatus, A. japonicus* or *Irpex lacteus* RGase DNA insert in any appropriate plasmid b) a DNA sequence which hybridizes to the coding region for the mature RGase DNA comprised by the DNA insert of a) and which comprises a structural gene for a polypeptide with RGase activity, and optionally a promoter, a coding region for a signal or leader peptide and/or transcriptional terminator c) a derivative of a DNA sequence defined in a) or b), or d) a DNA sequence which codes for a mature RGase or a signal peptide or a leader peptide thereof and which is degenerate within the meaning of the genetic code with respect to a DNA sequence of a) or b).

A preferred embodiment of the recombinant DNA sequence according to the invention is characterized by the fact that the RGase activity originates from the RGase producible by means of *Aspergillus aculeatus* CBS 101.43 with the partial amino acid sequence according to the invention.

A preferred embodiment of the recombinant DNA sequence according to the invention is characterized by the fact that the RGase activity originates from the RGase producible by means of *Aspergillus japonicus* ATCC 20236 with the partial amino acid sequence according to the invention.

A preferred embodiment of the recombinant DNA sequence according to the invention is characterized by the fact that the RGase activity originates from the RGase producible by means of *Irpex lacteus* ATCC 20157 with the partial amino acid sequence according to the invention.

Also, the invention comprises a vector, which comprises the recombinant DNA sequence according to the invention.

A preferred embodiment of the vector according to the invention is characterized by the fact that the promoter is the *Aspergillus oryzae* takaamylase promoter.

Also, the invention comprises a transformed host, which is characterized by the fact that it contains the vector according to the invention.

A preferred embodiment of the transformed host according to the invention is characterized by the fact that the transformed host is an Aspergillus strain.

A preferred embodiment of the transformed host according to the invention is characterized by the fact that the transformed host is a strain belonging to the species *Aspergillus aculeatus, Aspergillus niger, Aspergillus oryzae* or *Aspergillus awamori*.

A preferred embodiment of the transformed host according to the invention is characterized by the fact that the transformed host is a microorganism, which in its non-transformed condition does not produce RGase or only produces RGase in insignificant amounts, preferably *Bacillus sp., E. coli* or *S. cerevisiae*.

Also, the invention comprises a method for production of an RGase, which is characterized by the fact that a transformed host according to the invention is used for the production.

Also, the invention comprises an RGase which is produced by means of the method according to the invention.

Also, the invention comprises an enzyme preparation comprising the RGase according to the invention, which is characterized by the fact that it contains another plant cell wall degradation or modification agent, preferably a pectinase and/or cellulase and/or hemicellulase usable for degradation or modification of plant cell walls enriched with the RGase, preferably with an enrichment factor of at least 1.1 or deprived of an RGase, preferably with a deprivation factor of maximum 0.9.

A preferred embodiment of the enzyme preparation according to the invention is characterized by the fact that the other plant cell wall degradation or modification agent is producible by means of a microorganism belonging to the genus Aspergillus, preferably *Aspergillus niger, Aspergillus aculeatus, Aspergillus awamori* or *Aspergillus oryzae*.

Also, the invention comprises a use of the RGase according to the invention as an agent for degradation or modification of plant cell walls and/or plant cell wall components.

Also, the invention comprises a use of the enzyme preparation according to the invention as an agent for degradation or modification of plant cell walls and/or plant cell wall components.

In the following it will be explained in detail how the recombinant DNA sequence according to the invention can be produced.

The strain *Aspergillus aculeatus* CBS 101.43 as a gene donor was fermented in a pilot plant scale in the following way.

An agar substrate with the following composition was prepared in a Fernbach flask:

| | |
|---|---|
| Peptone Difco | 6 g |
| Aminolin Ortana | 4 g |
| Glucose | 1 g |
| Yeast extract Difco | 3 g |
| Meat extract Difco | 1.5 g |
| $KH_2PO_4$ Merck | 20 g |
| Malt extract Evers | 20 g |
| Ion exchanged $H_2O$ | ad 1000 ml | pH was adjusted to between 5.30 and 5.35. Then 40 g of Agar Difco was added, and the mixture was autoclaved for 20 minutes at 120° C. (the substrate is named E-agar).

The strain CBS 101.43 was cultivated on an E-agar slant (37° C.). The spores from the slant were suspended in sterilized skim-milk, and the suspension was lyophilized in vials. The contents of one lyophilized vial was transferred to the Fernbach flask. The flask was then incubated for 13 days at 30° C.

A substrate with the following composition was prepared in a 500 liter seed fermenter:

| | |
|---|---|
| $CaCO_3$ | 1.2 kg |
| Glucose | 7.2 kg |
| Rofec (corn steep liquor dry matter) | 3.6 kg |
| Soy bean oil | 1.2 kg |

Tap water was added to a total volume of around 240 liters. pH was adjusted to around 5.5 before addition of $CaCO_3$. The substrate was sterilized in the seed fermenter for 1 hour at 121 ° C. Final volume before inoculation was around 300 liters.

The Fernbach flask spore suspension was transferred to the seed fermenter. Seed fermentation conditions were:

Fermenter type: Conventional aerated and agitated fermenter with a height/diameter ratio of around 2.3.

| | |
|---|---|
| Agitation: | 300 rpm (two turbine impellers) |
| Aeration: | 300 normal liter air per minute |
| Temperature: | 30 to 31° C. |
| Time: | around 28 hours |

Around 28 hours after inoculation 150 liters was transferred from the seed fermenter to the main fermenter.

A substrate with the following composition was prepared in a 2500 liter main fermenter:

| | |
|---|---|
| Toasted soy meal | 90 kg |
| $KH_2PO_4$ | 20 kg |
| Pluronic ® antifoam agent | 150 ml |

Tap water was added to a total volume of around 900 liters. The toasted soy meal was suspended in water. pH was adjusted to 8.0 with NaOH, and the temperature was raised to 50° C. Thereafter around 925 Anson units of Alcalase® 0.6 L was added to the suspension. The mixture was held for 4 hours at 50° C. and pH=8.0 ($Na_2CO_3$ addition) with no aeration and 100 rpm agitation. Thereafter the remaining substrate components were added and pH was adjusted to around 6.0 with phosphoric acid. The substrate was sterilized in the main fermenter for 1½ hours at 123° C. Final volume before inoculation was around 1080 liters.

Then 150 liters of seed culture was added.

Fermentation conditions were:

Fermenter type: Conventional aerated and agitated fermenter with a height/diameter ratio of around 2.7.

| | |
|---|---|
| Agitation: | 250 rpm (two turbine impellers) |
| Aeration: | 1200 normal liter air per minute |
| Temperature: | 30° C. |
| Time: | around 151 hours |

From 24 fermentation hours to around 116 fermentation hours pectin solution was added aseptically to the main fermenter at a constant rate of around 8 liters per hour. The pectin solution with the following composition was prepared in a 500 liter dosing tank:

| | |
|---|---|
| Pectin genu*⁾ | 22 kg |
| Phosphoric acid, conc. | 6 kg |
| Pluronic ® antifoam agent | 50 ml |

*⁾Genu pectin (citrus type NF from the Copenhagen pectin factory Ltd.)

Tap water was added to a total volume of around 325 liters. The substrate was sterilized in the dosing tank for 1 hour at 121° C. Final volume before start of dosage was around 360 liters. When this portion ran out, another similar portion was made. Total volume of pectin solution for one fermentation was around 725 liters.

After around 151 fermentation hours the fermentation process was stopped. The around 1850 liters of culture broth were cooled to around 5° C. and the enzymes were recovered according to the following method.

The culture broth was drum filtered on a vacuum drum filter (Dorr Oliver), which was precoated with Hyflo Super-Cell diatomaceous earth (filter aid). The flitrate was concentrated by evaporation to around 15% of the volume of the culture broth. The concentrate was filtered on a Seitz filter sheet (type supra 100) with 0.25% Hyflo Super-Cell as a filter aid (in the following table referred to as filtration I). The flitrate was precipitated with 561 g of $(NH_4)_2SO_4$/l at a pH of 5.5, and 4% Hyfio Super-Cell diatomaceous earth is added as a filter aid. The precipitate and the filter aid are separated by filtration on a frame filter. The filter cake is dissolved in water, and insoluble parts are separated by filtration on a frame filter. The flitrate is check filtered on a Seitz filter sheet (type supra 100) with 0.25% Hyflo Super-Cell as a filter aid (in the following table referred to as filtration II). The flitrate is diafiltered on an ultrafiltration apparatus. After diafiltration the liquid is concentrated to a dry matter content of 12.7% (in the following table referred to as dry matter content in concentrate).

The RGase was isolated from the above indicated *Aspergillus aculeatus* enzyme preparation broth in the manner described in Table 1 (FIGS. 1–4).

TABLE 1

ASPERGILLUS ACULEATUS:
RHAMNOGALACTURONASE PURIFICATION

*Aspergillus aculeatus* enzyme broth
|
1: ULTRAFILTRATION - DIALYSIS
Filtron Minisette, filter area 3500 cm²,
membrane NMWL 10,000
20 mM TRIS, pH 5.0; 5 × volume TABLE 1-continued 2: IEC: WATER ACCELL QMA-PLUS, FIG. 1
(column: 5.0 × 23.0 cm, flow 60 ml/min)
eluent = 20 mM TRIS, pH 5.0, increasing NaCl-gradient
0.0M-linear-0.0125M-linear-0.25M-linear-0.5M 3: ULTRAFILTRATION - DIALYSIS
Filtron Minisette, filter area 3500 cm$^2$,
membrane NMWL 10,000
20 mM TRIS, pH 4.2; 5 × volume 4: CROSSLINKED ALGINATE, FIG. 2
(column, 4.9 × 17.5 cm, flow 10 ml/min)
eluent 1 = 20 mM TRIS, pH 4.2;
eluent 2 = 20 mM TRIS, pH 6.0

5: SAMPLE PREPARATION
crosslinked alginate pool, pH adjustment to 6.0

6: IEC: PROTEIN PAC DEAE-8 HR, FIG. 3
(column: 2.0 × 10.0 cm, flow 4.5 ml/min)
eluent: 20 mM TRIS, pH 6.0; increasing NaCl-gradient:
0.0M-step-0.038M-linear-0.1M-step-0.25M 7: ULTRAFILTRATION - DIALYSIS
Filtron minisette, filter area 1400 cm$^2$,
membrane NMWL 10,000
10 mM Na-phosphate buffer, pH 7.6; 5 × volume 8: HAC: HYDROXYLAPATITE BIOGEL HT, FIG. 4
(column: 4.9 × 11.0 cm, flow 25 ml/min)
eluent: Na-phosphate buffer, pH 7.6,
increasing gradient in molarity:
10 mM-linear-200 mM-step-500 mM

RHAMNOGALACTURONASE

TABLE 1-continued ad 1:
Buffer exchange in order to prepare for step 2, removal of small particles and about 50% of the colour, dilution to max. 15 mg protein/ml (otherwise the sample will not bind to the column in step 2).
ad 2:
IEC is ion exchange chromatography. The rhamnogalacturonase fraction was pooled from 0.04–0.08M NaCl.
ad 3:
Concentration and buffer exchange in order to prepare for step 4.
ad 4:
Affinity chromatography - the non retained fraction was pooled. The preparation of the crosslinked alginate was done according to Rombouts F. M., C. C. J. M. Geraeds, J. Visser, W. Pilnik, "Purification of various pectic enzymes on crosslinked polyuronides", in: Gribnau, T. C. J., J. Visser, R. J. F. Nivard (Editors), Affinity Chromatography and Related Techniques, Elsevier Scientific Publishing Company, Amsterdam, 255–260, 1982.
ad 5:
pH adaption in order to prepare for step 6.
ad 6:
HAC is hydroxylapatite chromatography. The rhamnogalacturonase fraction was pooled from 130 mM–160 mM NaH$_2$PO$_4$.
ad 7:
Concentration and buffer exchange in order to prepare for step 8.
ad 8:
IEC is ion exchange chromatography. The rhamnogalacturonase fraction was pooled from 55 mM–65mM NaCl.

Now a part of the amino acid sequence is determined:

The N-terminus of the RGase is blocked, and thus, direct amino acid sequencing is impossible. Following enzymatic digestion of the RGase with trypsin the following internal amino acid sequences have been obtained. Xaa designates undetermined amino acid residues that most likely carry carbohydrate.

Tryp-19:

```
1               5               10              15                    (SEQ ID NO: 1)
Gly—Ala—Val—Gln—Gly—Phe—Gly—Tyr—Val—Tyr—His—Ala—Glu—Gly—Thr

Tyr—Gly—Ala—Arg
```

Tryp-23:

```
1               5               10              15                    (SEQ ID NO: 2)
Ser—Xaa—Asn—Ile—Leu—Ser—Tyr—Gly—Ala—Val—Ala—Asp—Xaa—Ser—Thr—

20              25
Asp—Val—Gly—Pro—Ala—Ile—Thr—Ser—Ala—Xaa—Ala—Ala—Arg—Lys
```

```
1                                                                      (SEQ ID NO: 3)
Ser—Arg—Asn—Ile
```

```
1               5               10                                     (SEQ ID NO: 4)
Ser—Ala—Tyr—Gly—Ser—Gly—Tyr—Xaa—Leu—Lys
```

```
1               5                                                      (SEQ ID NO: 5)
Thr—Leu—Glu—Asp—Ile—Ala—Ile
```

```
1               5               10              15                     (SEQ ID NO: 6)
Gly—Leu—Xaa—Ala—Xaa—Ile—Pro—Ile—Pro—Xaa—Ile—Pro—Pro—Xaa—Phe—

Phe
```

| | |
|---|---|
| Molecular weight: | 61,000 Dalton |
| Isoelectric point: | pH 4.6 |

The RGase activity unit which is the same for *A. aculeatus* RGase, *A. japonicus* RGase and *Irpex lacteus* RGase, is defined as follows.

1 unit of RGase is the amount of enzyme which at pH 5, 30° C. and in 1 minute releases 1µmole of molecules from Saponified Modified Hairy Regions (MHR-S) from apples as substrate.

This MHR-S substrate was made according to the method described in Schols et al. in Carbohydrate Research 206 (1990), pages 105–115, "Rhamnogalacturonase: a novel enzyme, that degrades the hairy regions of pectins".

The release of molecules is calculated from the change in distribution of molecular weights determined with High Performance Gel Permeation Chromatography (HPGPC). Using commercial Gel Permeation Chromatography software, the Number Average Molecular Weight ($M_n$) was calculated before and after treatment with RGase. In relation to the substrate concentration, the number of glycosidic linkages cleaved were calculated and expressed in activity units according to the above mentioned unit definition.

The strain *Aspergillus japonicus* ATCC 20236 as a gene donor was fermented in a pilot plant scale in the following way.

An agar substrate with the following composition was prepared in a Fernbach flask:

| | |
|---|---|
| Peptone Difco | 6 g |
| Aminolin Ortana | 4 g |
| Glucose | 1 g |
| Yeast extract Difco | 3 g |
| Meat extract Difco | 1.5 g |
| $KH_2PO_4$ Merck | 20 g |
| Malt extract Evers | 20 g |
| Ion exchanged $H_2O$ | ad 1000 ml |

```
1                5
Ser—Leu—Asp—Ile—Asp—Gly—Tyr 1                5              10
Ser—Val—His—Asp—Ile—Ile—Leu—Val—Asp—Ala—Pro—Ala—Phe 1              5
Ala—Ala—Asp—Leu—Ala—

1
Gly—Ser—Asn—Ile 1              5
Tyr—Pro—Gly—Leu—Thr—Pro—Tyr 1              5                10
Asn—Val—Tyr—Thr—Trp—Ser—Ser—Asn—Gln—Met—Tyr—Met—Ile—Lys
```

(SEQ ID NO: 7)

(SEQ ID NO: 8)

(SEQ ID NO: 9)

(SEQ ID NO: 10)

(SEQ ID NO: 11)

(SEQ ID NO: 12)

The *Aspergillus aculeatus* RGase was further characterized, as follows.

Figure 1:
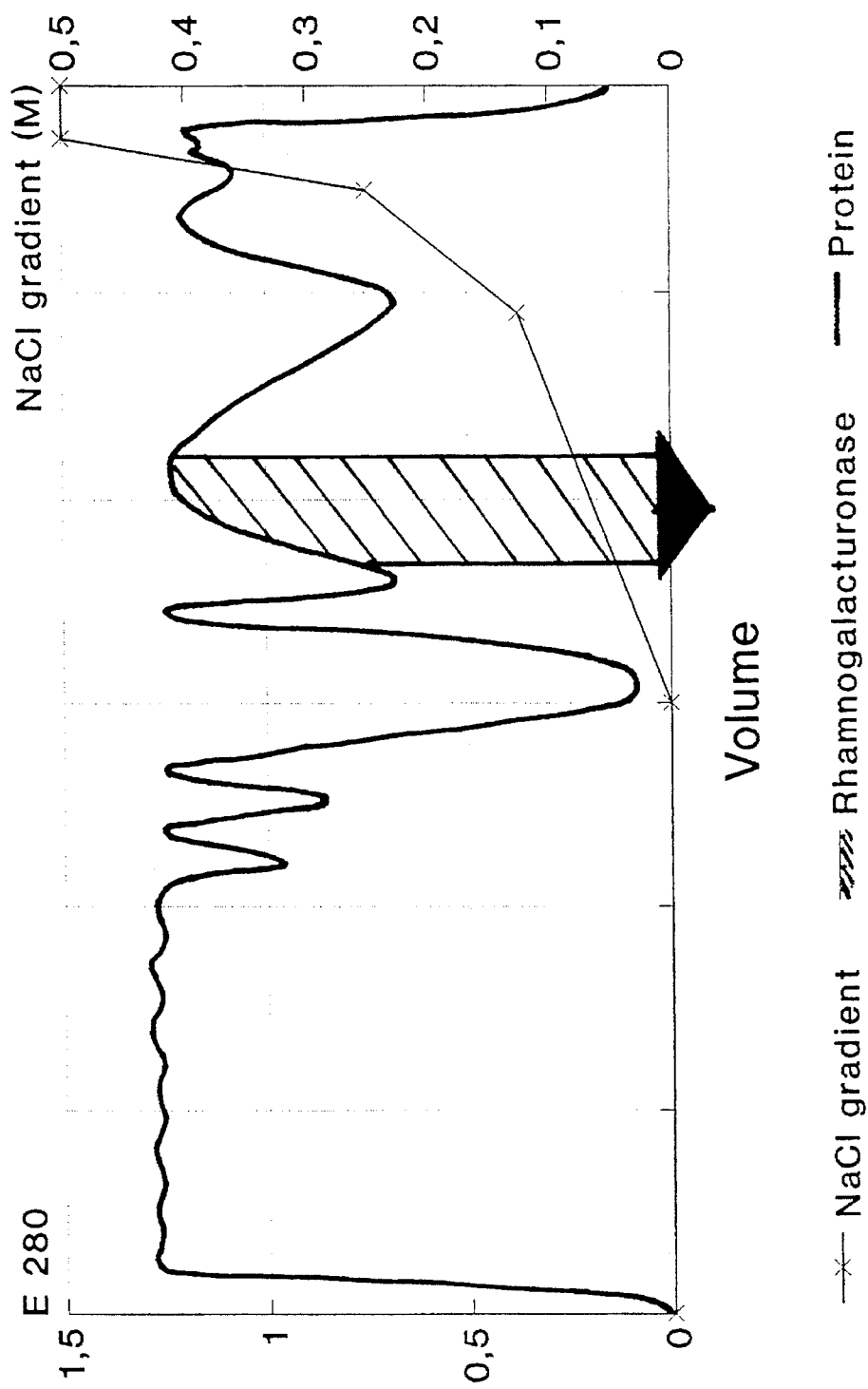
FIG. 1 shows an ion exchange chromatogram of the process for purifying an *Aspergillus aculeatus* rhamnogalacturonase.
Figure 2:
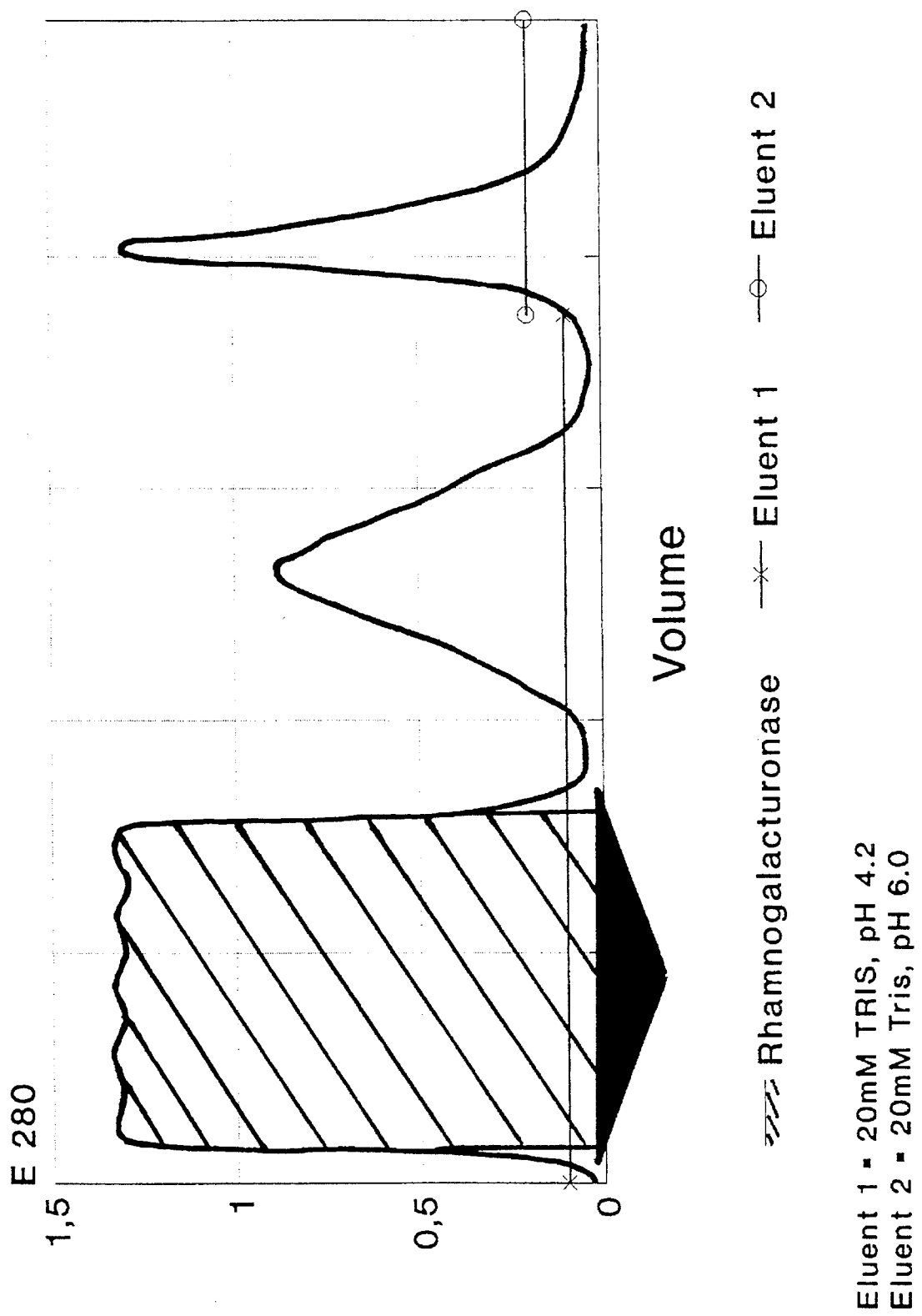
FIG. 2 shows an affinity chromatogram of the process for purifying an *Aspergillus aculeatus* rhamnogalacturonase.
Figure 3:
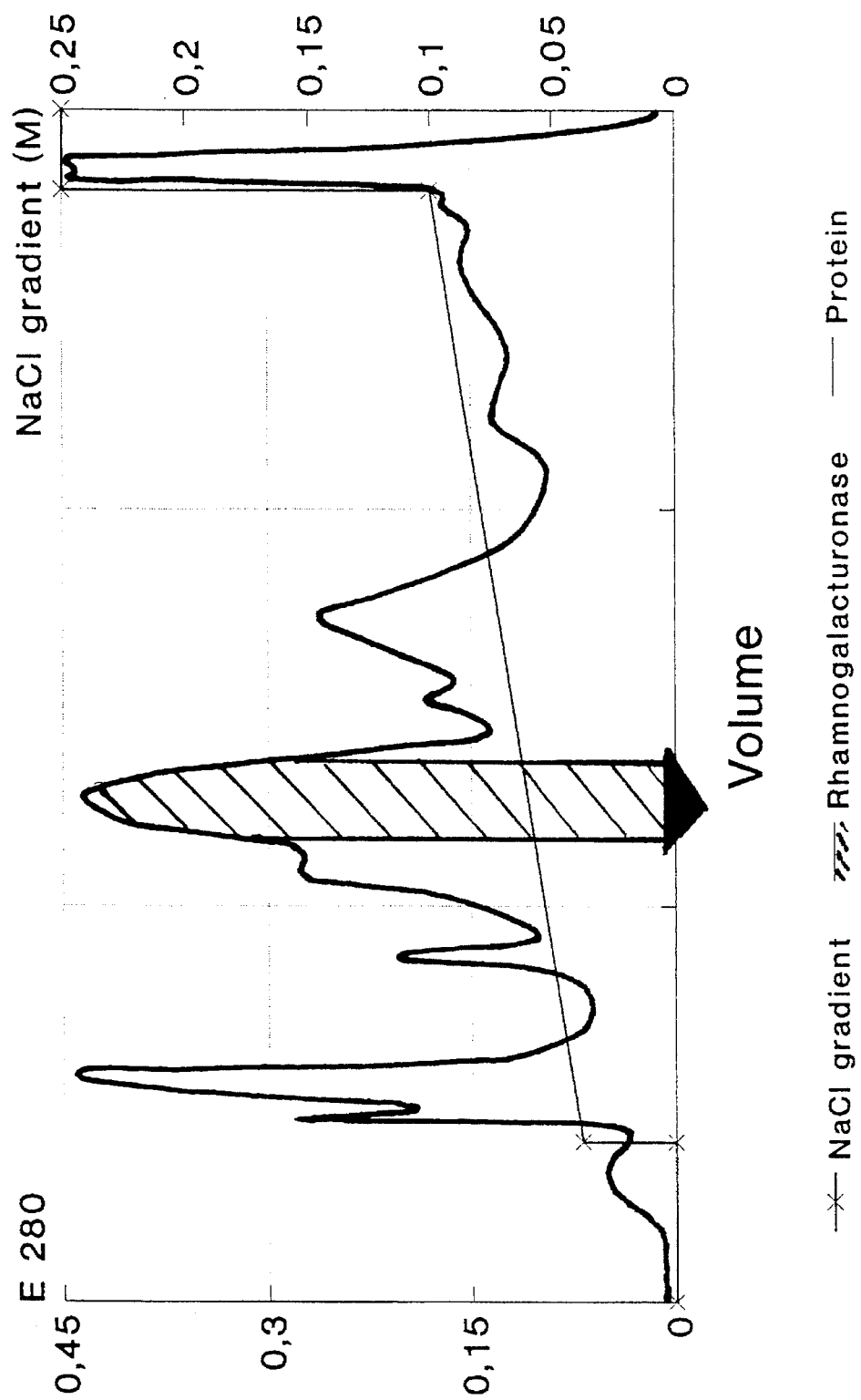
FIG. 3 shows an ion exchange chromatogram of the process for purifying an *Aspergillus aculeatus* rhamnogalacturonase.
Figure 4:
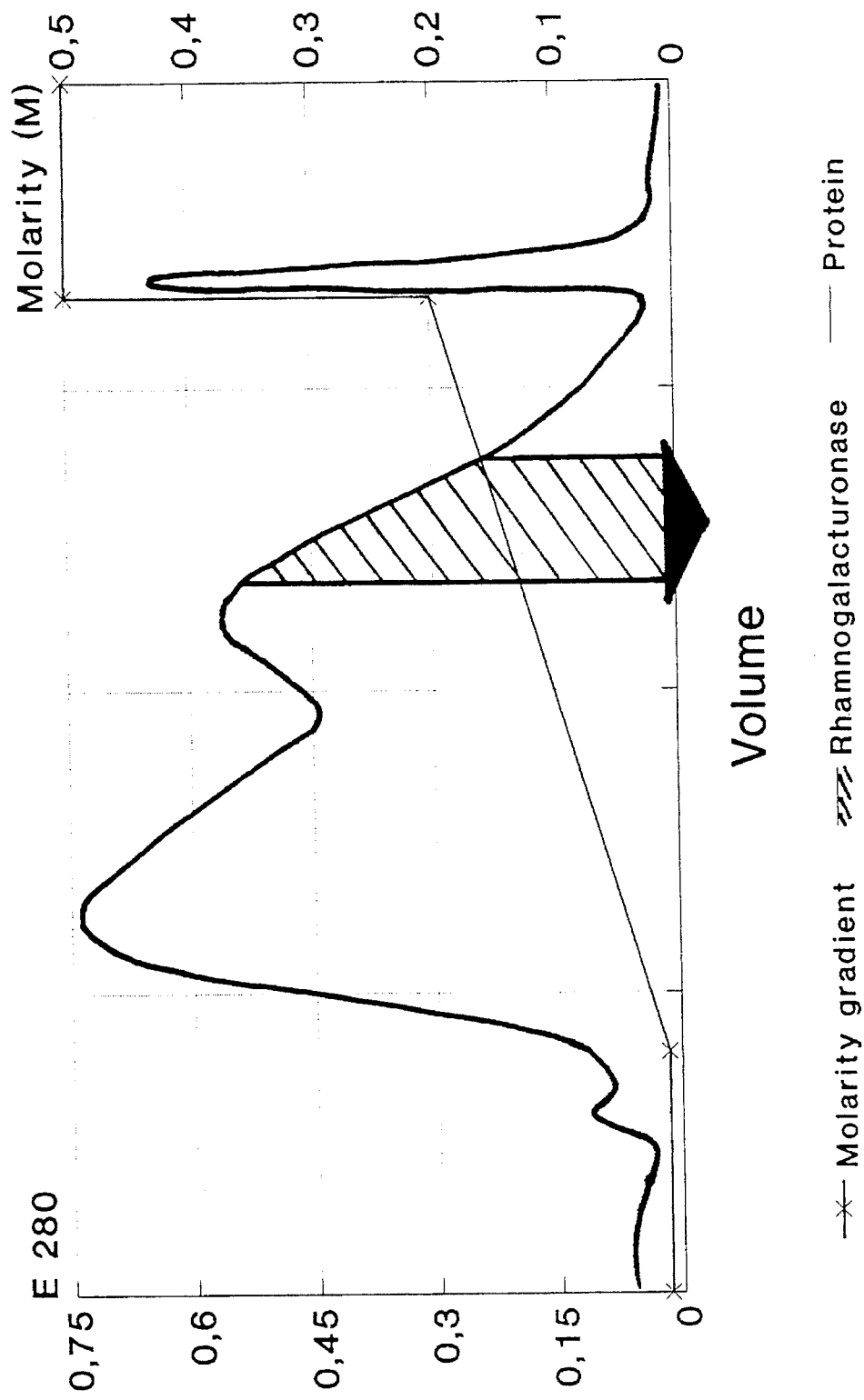
FIG. 4 shows a hydroxyapatite chromatogram of the process for purifying an *Aspergillus aculeatus* rhamnogalacturonase.
Figure 5:
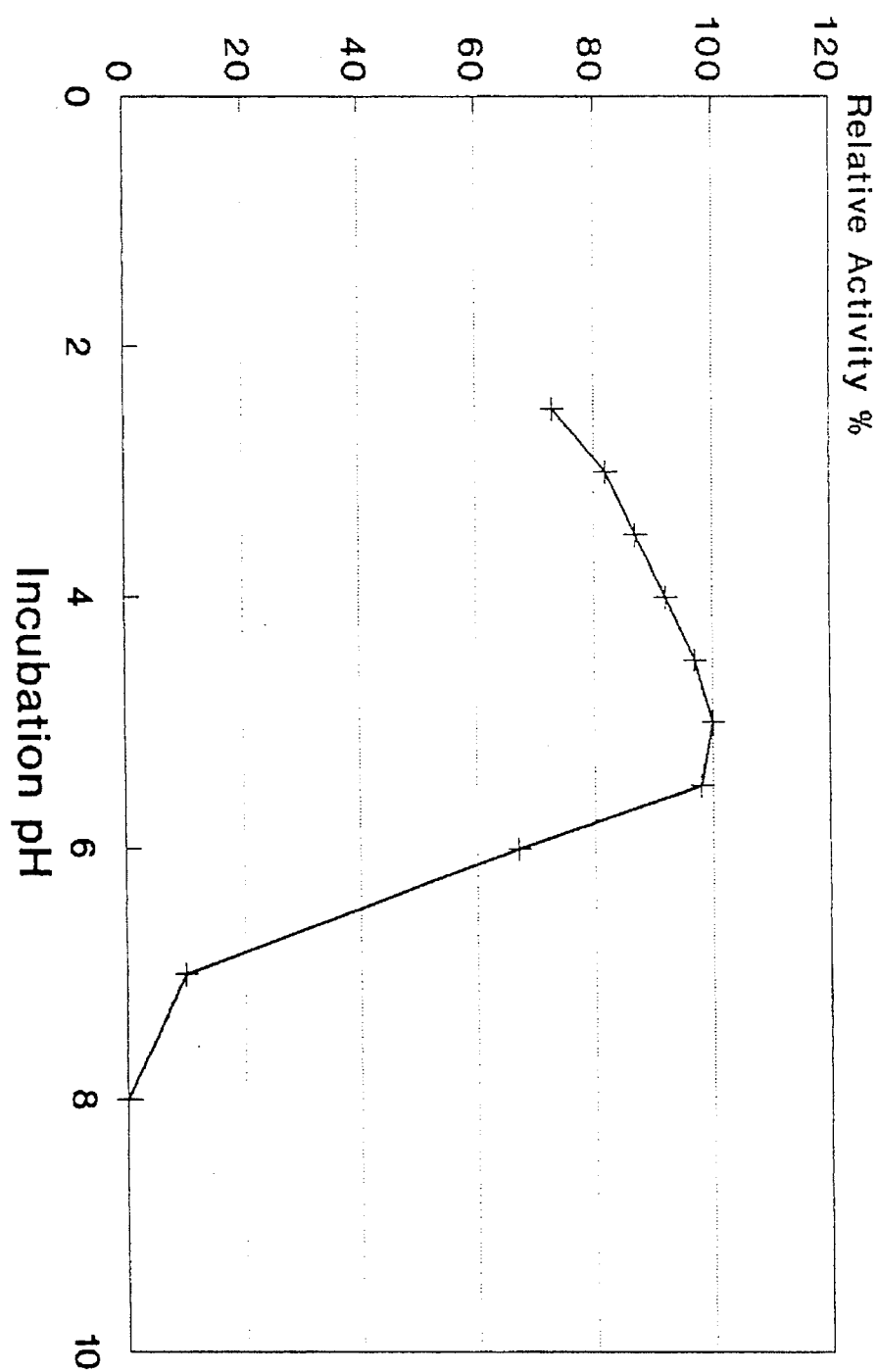
FIG. 5 shows the pH activity of an *Aspergillus aculeatus* rhamnogalacturonase.
Figure 6:
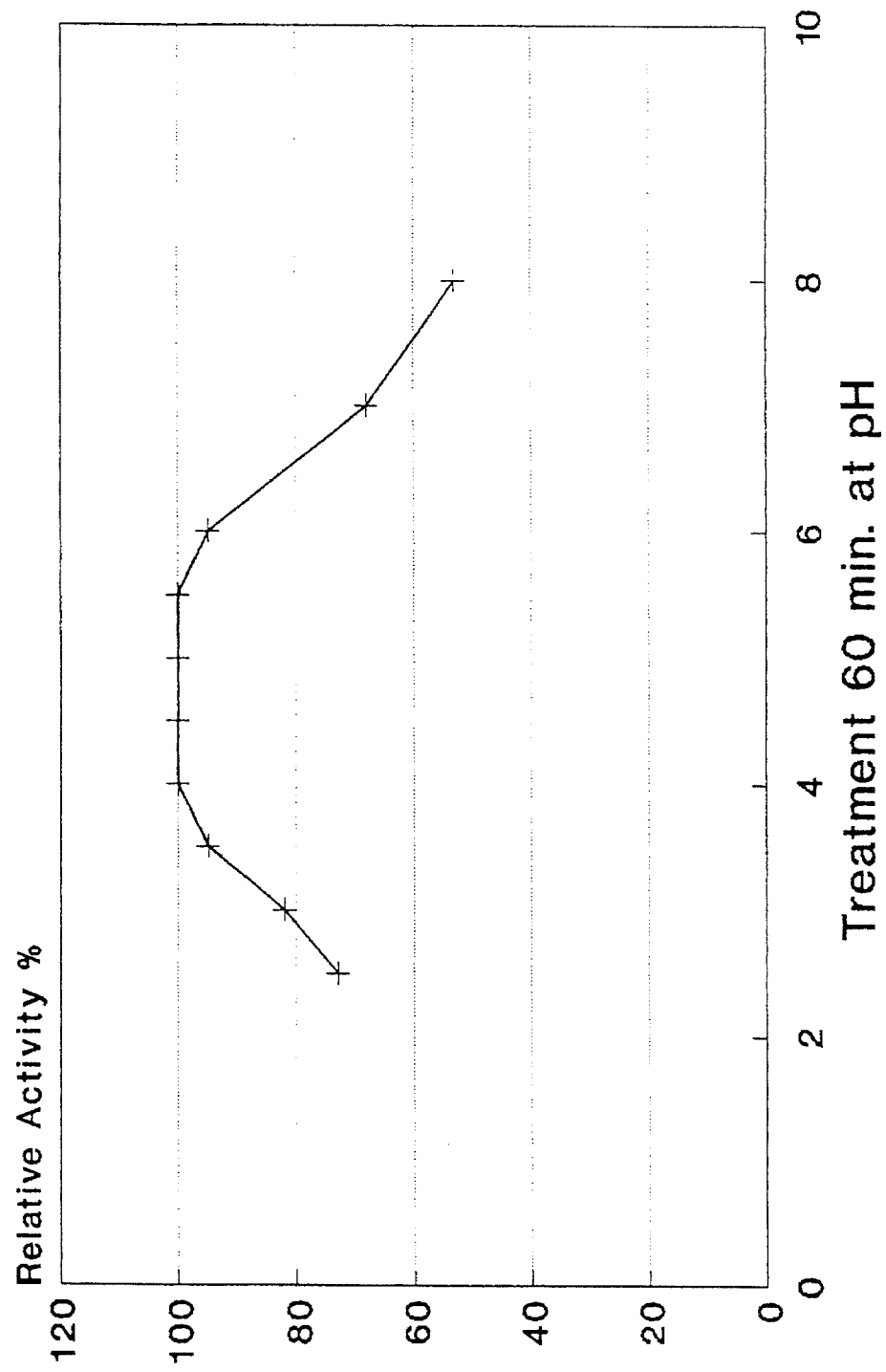
FIG. 6 shows the pH stability of an *Aspergillus aculeatus* rhamnogalacturonase.

FIGS. 5 and 6 show the pH activity and pH stability, respectively.

The pH-optimum is around pH 5.0. The stability is good between pH 3 and 6.5 (>80% residual activity), when treated for 1 hour at room temperature. The activity decreases slightly in the more acidic range; at pH 2.5 still around 70% of activity is found.

Figure 7:
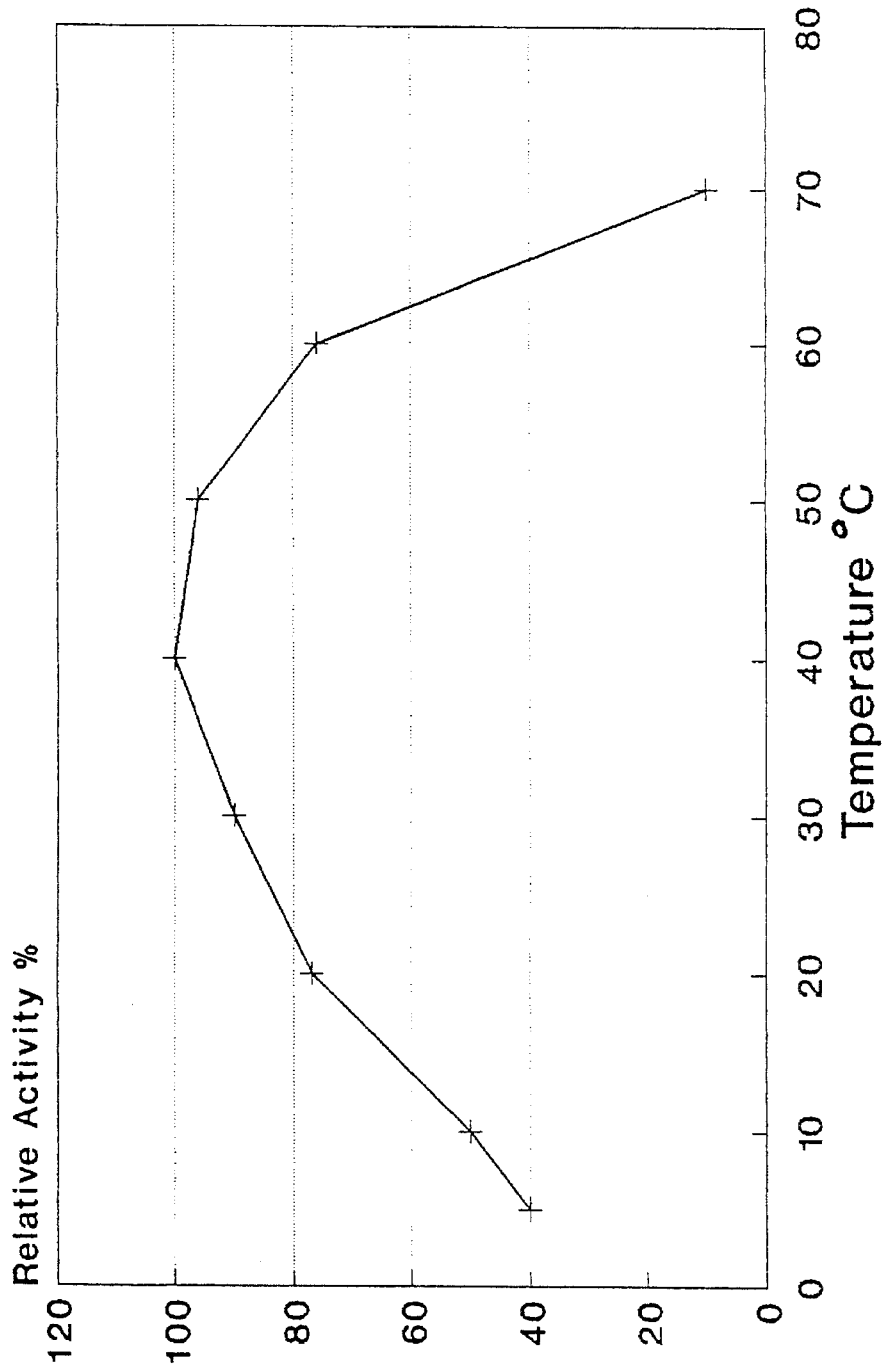
FIG. 7 shows the temperature activity of an *Aspergillus aculeatus* rhamnogalacturonase.
Figure 8:
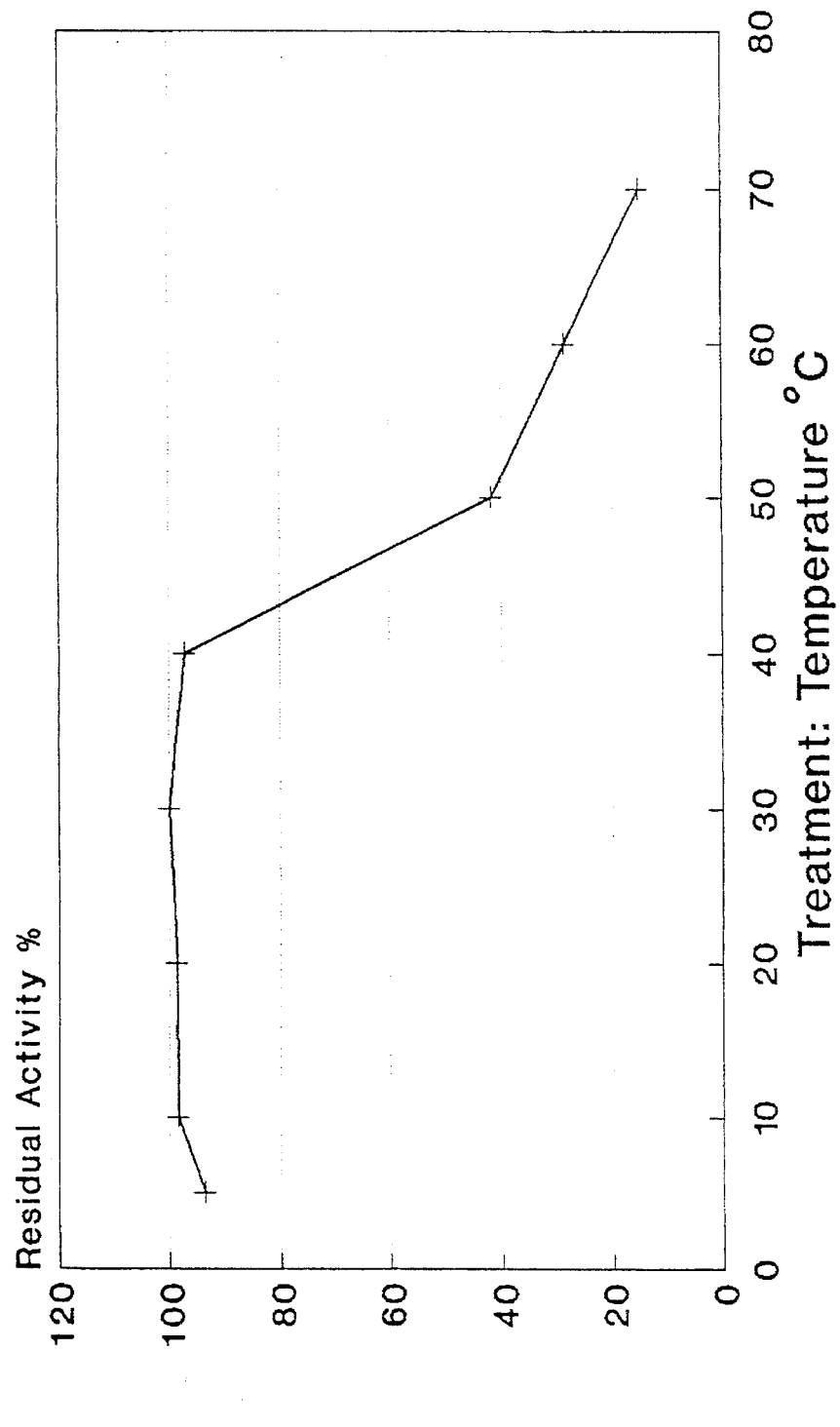
FIG. 8 shows the temperature stability of an *Aspergillus aculeatus* rhamnogalacturonase.

FIGS. 7 and 8 shows the temperature activity dependency and the temperature stability dependency, respectively.

The temperature optimum is around 40° C., and the temperature activity range is relatively broad. For the fruit juice and wine industry the activity in the low temperature range is very remarkable: Around 50% activity at 10° C., and around 40% activity at 5° C.

In the temperature range of 5°–50° C. this RGase is not remarkably influenced after a treatment of 1 hour at pH 4.5 (>80% of the initial activity), but rapidly inactivated at temperatures above 55° C.

pH was adjusted to between 5.30 and 5.35. Then 40 g of Difco agar was added, and the mixture was autoclaved for 20 minutes at 120° C. (the substrate is named E-agar).

The strain ATCC 20236 was cultivated on an E-agar slant (30° C.). The spores from the slant were suspended in sterilized skim milk, and the suspension was lyophilized in vials. The contents of one lyophilized vial was transferred to the Fernbach flask. The flask was then incubated for 27 days at 30° C.

A substrate with the following composition was prepared in a 500 liter seed fermenter:

| | |
|---|---|
| $CaCO_3$ | 1.2 kg |
| Glucose | 7.2 kg |
| Rofec (corn steep liquor dry matter) | 3.6 kg |
| Soy bean oil | 1.2 kg |

Tap water was added to a total volume of around 240 liters. pH was adjusted to around 5.5 before addition of $CaCO_3$. The substrate was sterilized in the seed fermenter for 1 hour at 121° C. The final volume before inoculation was around 300 liters.

The Fernbach flask spore suspension was transferred to the seed o fermenter. Seed fermentation conditions were:

Fermenter type: Conventional aerated and agitated fermenter with a height/diameter ratio of around 2.3.

| | |
|---|---|
| Agitation: | 300 rpm (two turbine impellers) |
| Aeration: | 300 normal liter air per minute |
| Temperature: | 30 to 31° C. |
| Time: | around 28 hours |

Around 28 hours after inoculation 150 liters was transferred from the seed fermenter to the main fermenter.

A substrate with the following composition was prepared in a 2500 liter main fermenter:

| | |
|---|---|
| Toasted soy meal | 90 kg |
| $KH_2PO_4$ | 20 kg |
| Pluronic ® antifoam agent | 150 ml |

Tap water was added to a total volume of around 900 liters. The toasted soy meal was suspended in water. pH was adjusted to 8.0 with NaOH, and the temperature was raised to 50° C. Thereafter around 925 Anson units of Alcalase® 0.6 L was added to the suspension. The mixture was held for 4 hours at 50° C and pH=8.0 ($Na_2CO_3$ addition) with no aeration and 100 rpm agitation. Thereafter the remaining substrate components were added and pH was adjusted to around 6.0 with phosphoric acid. The substrate was sterilized in the main fermenter for 1½ hours at 123° C. The final volume before inoculation was around 1100 liters.

Then 150 liters of seed culture was added.

Fermentation conditions were:

Fermenter type: Conventional aerated and agitated fermenter with a height/diameter ratio of around 2.7.

| Agitation: | 250 rpm (two turbine impellers) |
|---|---|
| Aeration: | 1200 normal liters of air per minute |
| Temperature: | 30° C. |
| Time: | around 151 hours |

From 24 fermentation hours to around 130 fermentation hours pectin solution was added aseptically to the main fermenter at a constant rate of around 8 liters per hour. The pectin solution with the following composition was prepared in a 500 liter dosing tank:

| Pectin genu*) | 22 kg |
|---|---|
| Phosphoric acid, conc. | 6 kg |
| Pluronic ® antifoam agent | 50 ml |

*)Genu pectin was of the citrus type NF from the Copenhagen pectin factory Ltd.

Tap water was added to a total volume of around 325 liters. The substrate was sterilized in the dosing tank for 1 hour at 121° C. The final volume before start of dosage was around 360 liters. When this portion ran out, another similar portion was made.

After around 151 fermentation hours the fermentation process was stopped. The resulting culture broth with a volume of approximately 1850 liters was cooled to around 5° C., and the enzymes were recovered according to the following method.

The culture broth was drum filtered on a vacuum drum filter (Dorr Oliver), which was precoated with Hyflo Super-Cell diatomaceous earth (filter aid). The fiitrate was concentrated by evaporation to around 15% of the volume of the culture broth. The concentrate was filtered on a Seitz filter sheet (type supra 100) with 0.25% Hyflo Super-Cell as a filter aid. The flitrate was precipitated with $(NH_4)_2SO_4$ at a pH of 5.5, and 4% Hyflo Super-Cell diatomaceous earth is added as a filter aid. The precipitate and the filter aid are separated by filtration on a frame filter. The filter cake is dissolved in water, and insoluble parts are separated by filtration on a frame filter. The flitrate is check filtered on a Seitz filter sheet (type supra 100) with 0.25% Hyflo Super-Cell as a filter aid. The flitrate is diafiltered on an ultrafiltration apparatus. After diafiltration the liquid is concentrated.

TABLE 2

*ASPERGILLUS JAPONICUS*:
RHAMNOGALACTURONASE PURIFICATION

*Aspergillus japonicus* enzyme broth
|
1: ULTRAFILTRATION - DIALYSIS
Filtron Minisette, filter area 3500 $cm^2$,
membrane NMWL 10,000
20 mM TRIS, pH 6,0; 5 × volume
|
2: IEC: WATER ACCELL QMA-PLUS, FIG. 9
(column: 5.0 × 26.5 cm, flow 60 ml/min)
eluent = 20 mM TRIS, pH 6.0, increasing NaCl-gradient:
0.0M-step-0.05M-linear-0.225M-linear-0.35M-step-0.5M
|
3: SAMPLE PREPARATION
Rhamnogalacturonase pool, addition of solid $(NH_4)_2SO_4$
to 2M concentration, pH-adjustment to pH 5.0
|
4: HIC: PHENYL TOYOPEARL 650 (M), FIG. 10
(column: 2.6 × 23.0 cm, flow 16 ml/min)
eluent: water, decreasing $(NH_4)_2SO_4$ gradient:
2M-concave decrease
(=linear decrease of conductivity)-0.5M-step-0.0M
|
5: ULTRAFILTRATION - DIALYSIS
Filtron Minisette, filter area 1400 $cm^2$,
membrane NMWL 10,000
10 mM TRIS-buffer, pH 5.0; 5 × volume
|
6: IEC: PROTEIN PAC DEAE-8 HR, FIG. 11
(column: 2.0 × 10.0 cm, flow 4.5 ml/min)
eluent: 10 mM TRIS, pH 5.0; increasing NaCl-gradient:
0.0M - linear - 0.15M
|
RHAMNOGALACTURONASE ad 1:
Buffer exchange in order to prepare for step 2, removal of small particles and about 50% of the colour, dilution to maximum 15 mg protein/ml (otherwise the sample will not bind to the column in step 2).
ad 2:
IEC is ion exchange chromatography. The rhamnogalacturonase fraction was pooled from 0.05 to 0.06M NaCl.
ad 3:
Buffer adaption in order to prepare for step 4.
ad 4:
HIC is hydrophobic interaction chromatography. The rhamnogalacturonase fraction was pooled from 1.18 to 1.41M $(NH_4)_2SO_4$.
ad 5:
Buffer exchange in order to prepare for step 6.
ad 6:
IEC is ion exchange chromatography. The rhamnogalacturonase fraction was pooled from 0.014 to 0.024M NaCl.

Now a part of the amino acid sequence is determined, i.e. the N-terminal amino acid sequence of the rhamnogalacturonase from *Aspergillus japonicus* ATCC 20236.

```
 1           5            10            15        (SEQ ID NO: 13)
Ala—Phe—Gly—Ile—Thr—Thr—Ser—Ser—Ser—Ala—Tyr—Val—Ile—Asp—Thr—
                    20                    25
         Asp—Ala—Pro—Asn—Gln—Leu—Lys—Xaa—Thr—Val—Ser—Arg
```

Figure 9:
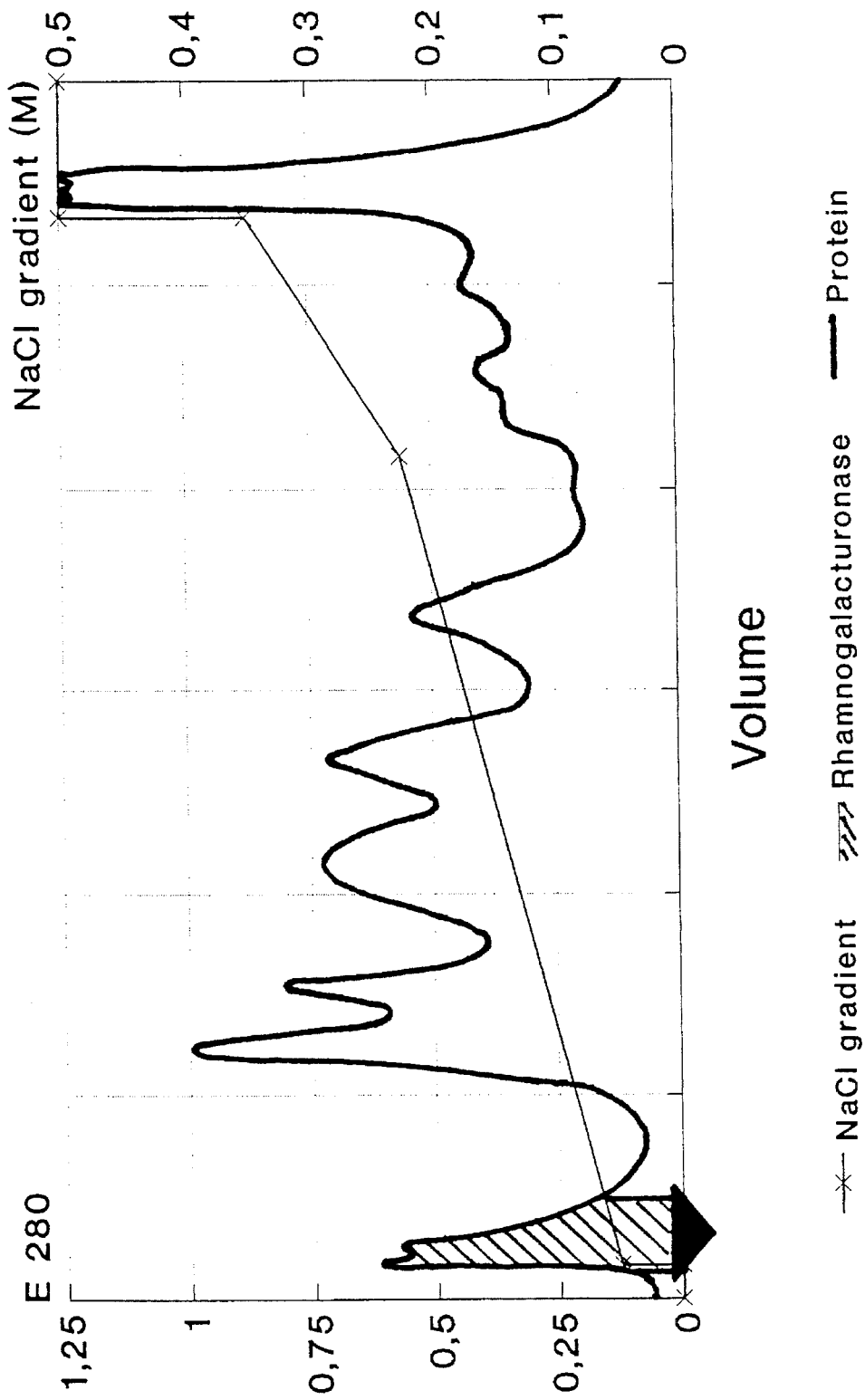
FIG. 9 shows an ion exchange chromatogram of the process for purifying an *Aspergillus japonicus* rhamnogalacturonase.
Figure 10:
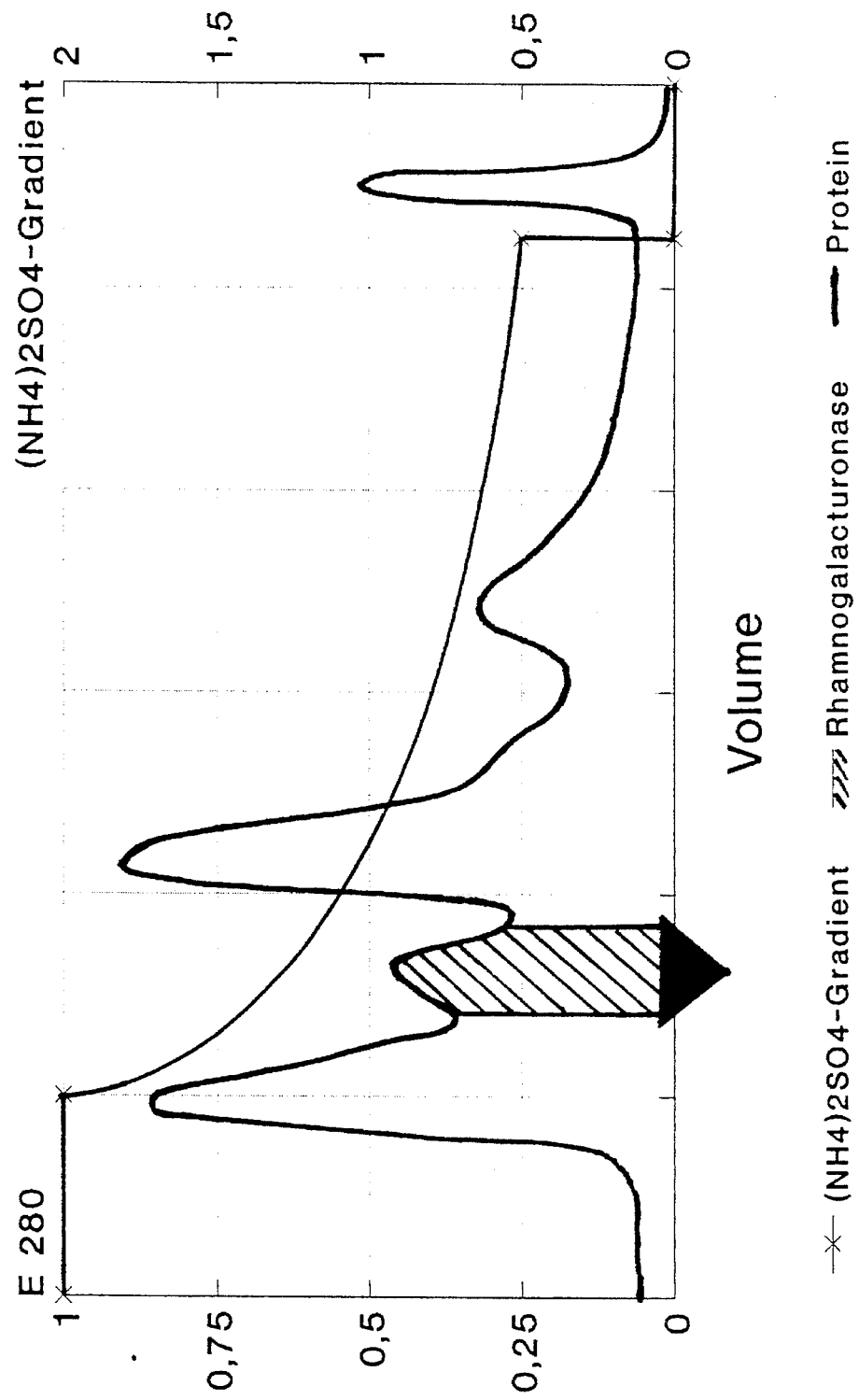
FIG. 10 shows a hydrophobic interaction chromatogram of the process for purifying an *Aspergillus japonicus* rhamnogalacturonase.
Figure 11:
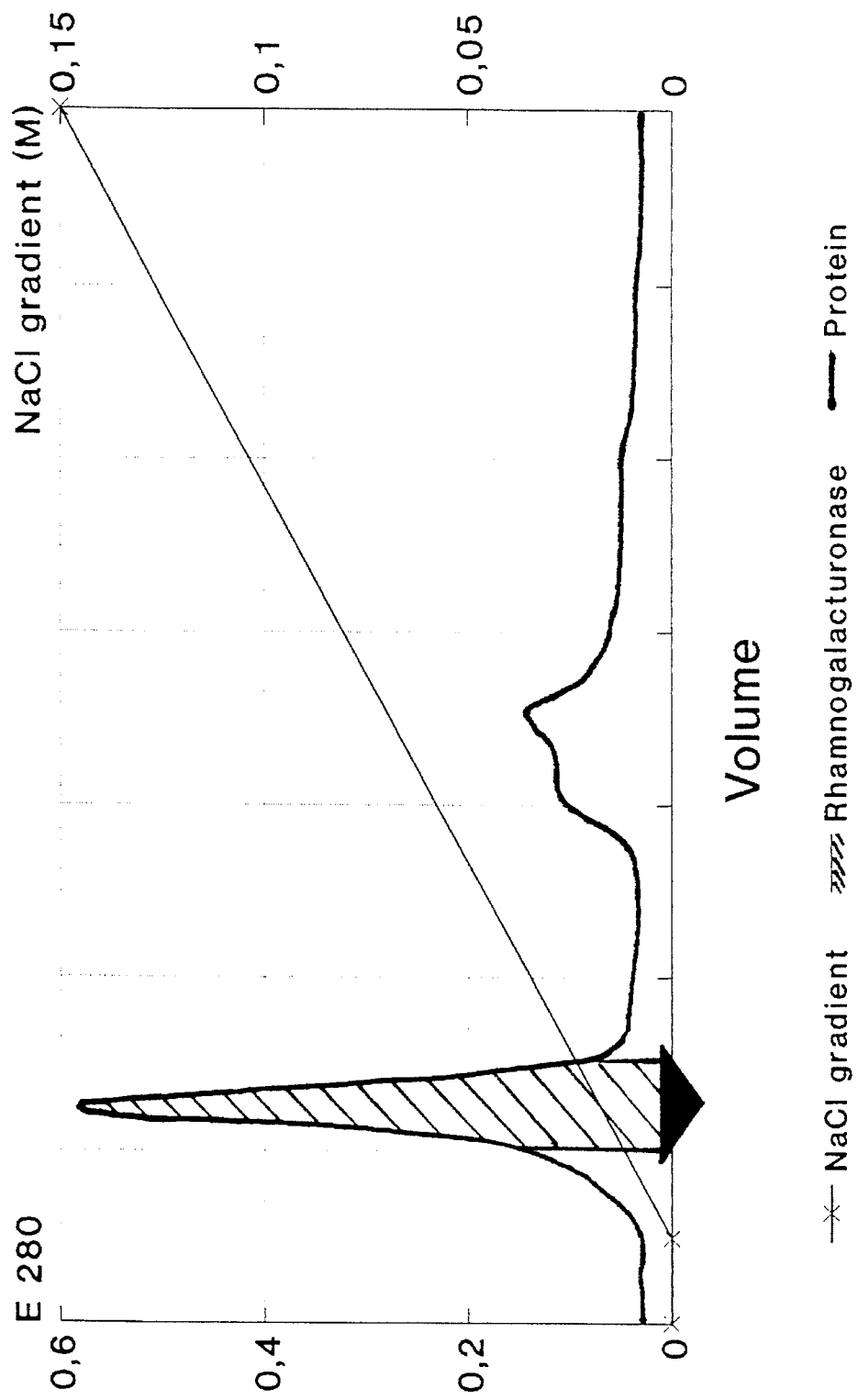
FIG. 11 shows an ion exchange chromatogram of the process for purifying an *Aspergillus japonicus* rhamnogalacturonase.

The RGase was isolated from the above indicated *Aspergillus japonicus* enzyme preparation in the manner described in Table 2 (FIGS. 9–11).

The sequence has no homology to other proteins in the databases. In addition, there is no homology to the peptide sequences from the rhamnogalacturonase from *Aspergillus aculeatus*.

The *Aspergillus japonicus* RGase was further characterized, as follows.

Figure 12:
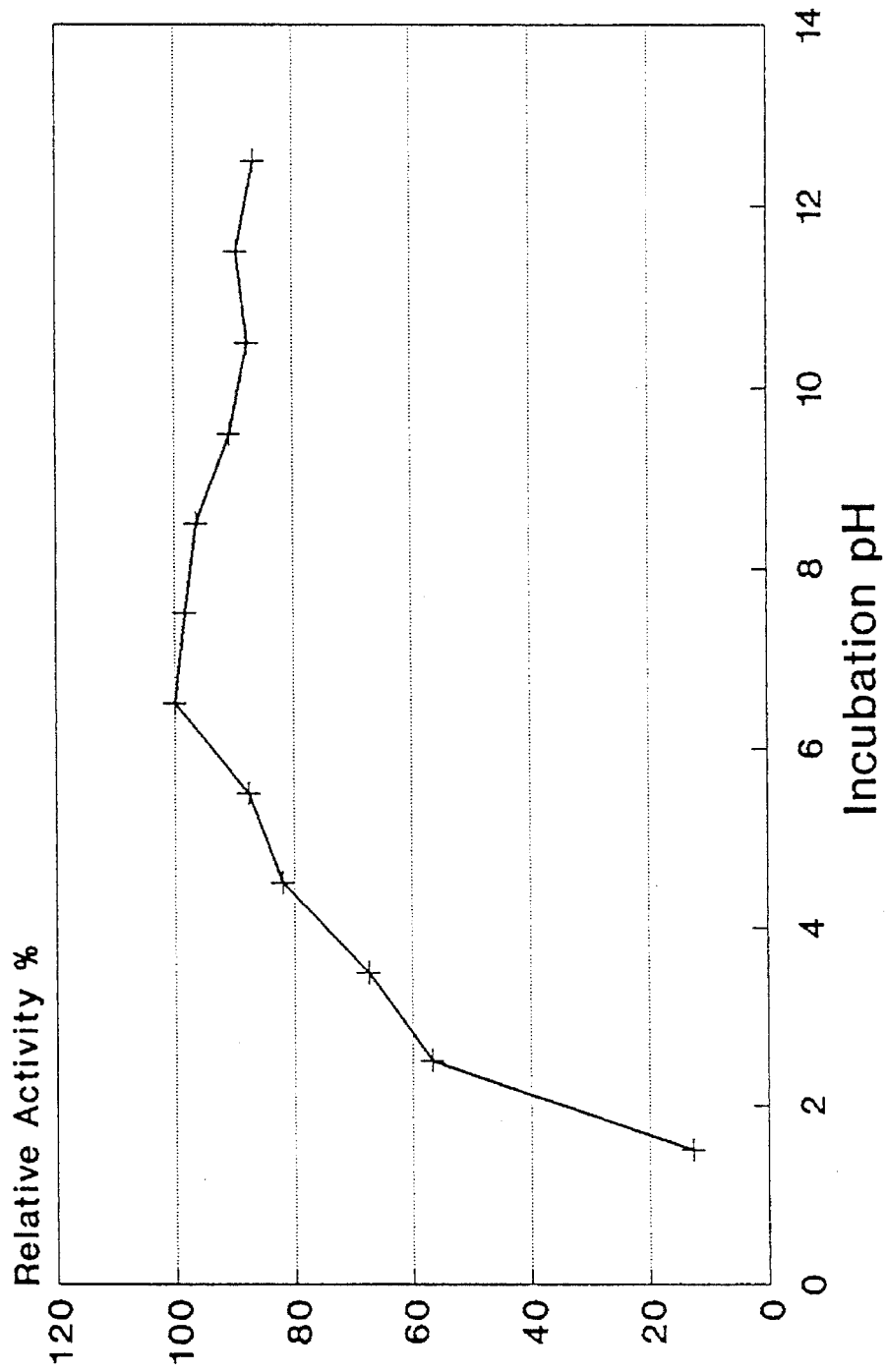
FIG. 12 shows the pH activity of an *Aspergillus japonicus* rhamnogalacturonase.
Figure 13:
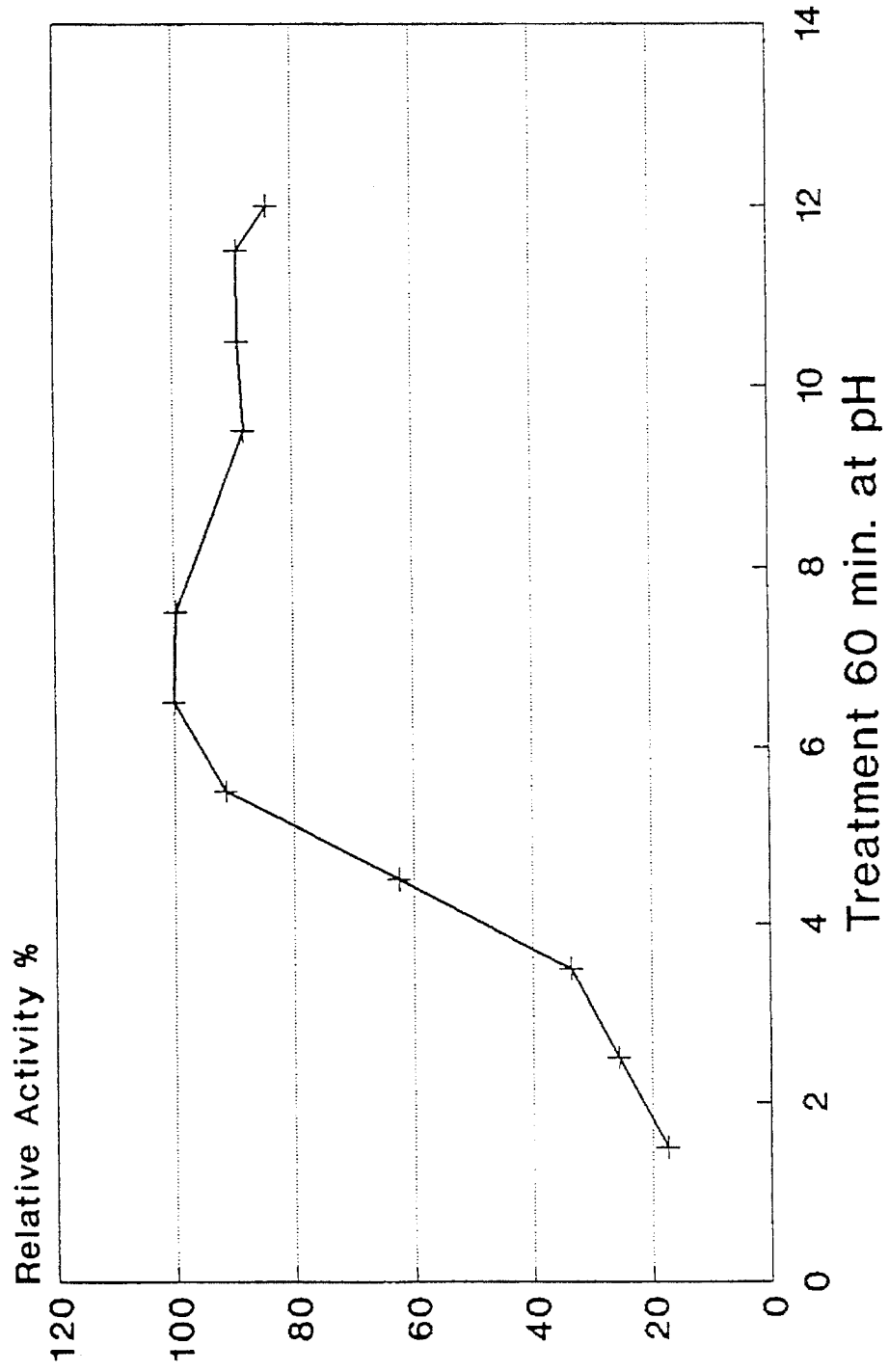
FIG. 13 shows the pH stability of an *Aspergillus japonicus* rhamnogalacturonase.

FIGS. 12 and 13 show the pH activity and pH stability, respectively.

The pH-optimum is around pH 6.5–7.0. Especially remarkable is the activity in the neutral and alkaline range: between pH 5.5 and 12 the activity is >80% of the maximum activity.

The stability is good between pH 5.5 and 12, when treated for 1 hour at room temperature, whereas at lower pH the stability decreases significantly.

Figure 14:
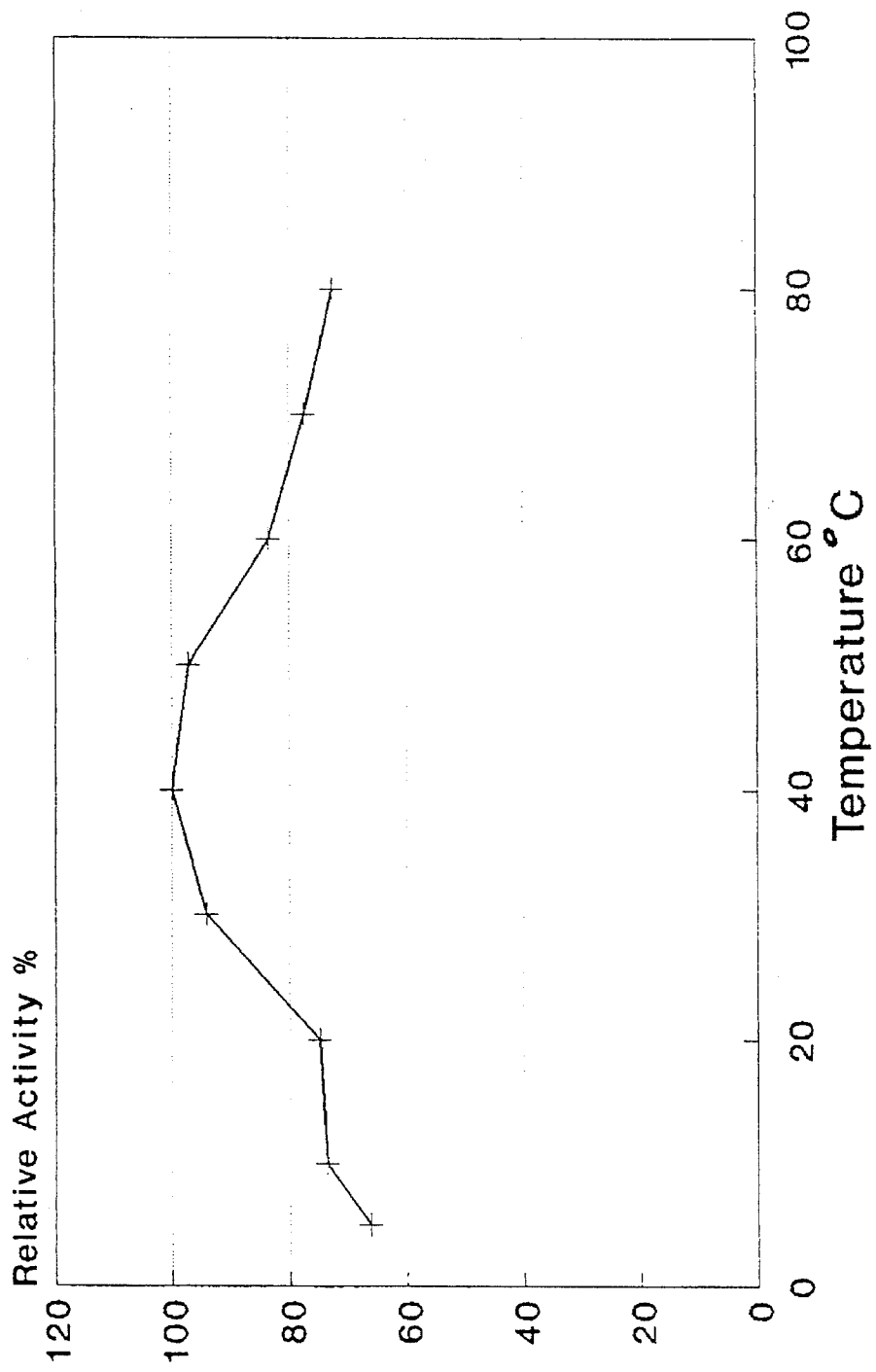
FIG. 14 shows the temperature activity of an *Aspergillus japonicus* rhamnogalacturonase.
Figure 15:
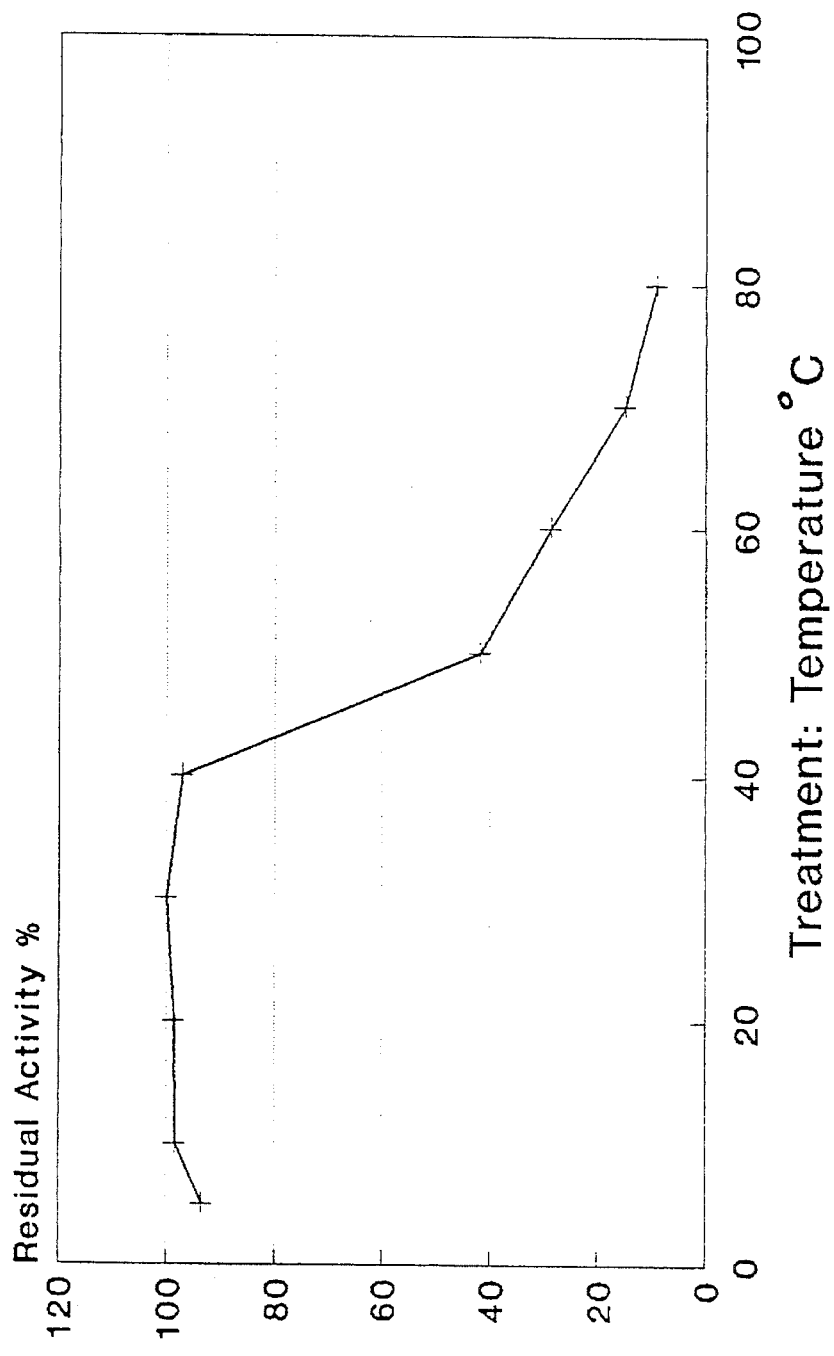
FIG. 15 shows the temperature stability of an *Aspergillus japonicus* rhamnogalacturonase.

FIGS. 14 and 15 show the temperature activity dependency and the temperature stability dependency, respectively.

The temperature optimum is around 40° C., and the temperature activity range is relatively broad: between 20° and 60° C. the activity is >80% of the maximum activity.

For the fruit juice and wine industry the activity in the low temperature range is very remarkable: >60% activity at 5°–10° C. In the temperature range of 5°–40° C. this RGase is not remarkably influenced after a treatment of 1 hour at pH 4.5 (>80% of the initial activity); but above 40° C. it is remarkably influenced.

| Molecular weight: | 53,000 Dalton |
|---|---|
| Isoelectric point: | pH 5.3 |

The strain *Irpex lacteus* ATCC 20157 as a gene donor was fermented in a pilot plant scale in the following way.

An agar substrate with the following composition was prepared in a Fernbach flask:

| Peptone Difco | 6 g |
|---|---|
| Aminolin Ortana | 4 g |
| Glucose | 1 g |
| Yeast extract Difco | 3 g |
| Meat extract Difco | 1.5 g |
| KH$_2$PO$_4$ Merck | 20 g |
| Malt extract Evers | 20 g |
| Ion exchanged H$_2$O | ad 1000 ml | pH was adjusted to between 5.30 and 5.35. Then 40 g of Difco agar was added, and the mixture was autoclaved for 20 minutes at 120° C. (the substrate is named E-agar).

The strain ATCC 20157 was cultivated on an E-agar slant (37° C.). The spores from the slant were suspended in sterilized skim milk, and the suspension was lyophilized in vials. The contents of one lyophilized vial was transferred to the Fernbach flask. The flask was then incubated for 18 days at 37° C.

A substrate with the following composition was prepared in a 500 liter seed fermenter:

| CaCO$_3$ | 1.2 kg |
|---|---|
| Glucose | 7.2 kg |
| Rofec (corn steep liquor dry matter) | 3.6 kg |
| Soy bean oil | 1.2 kg |

Tap water was added to a total volume of around 240 liters. pH was adjusted to around 5.5 before addition of CaCO$_3$. The substrate was sterilized in the seed fermenter for 1 hour at 1 21 ° C. The final volume before inoculation was around 300 liters.

The Fernbach flask spore suspension was transferred to the seed fermenter. The seed fermentation conditions were:

Fermenter type: Conventional aerated and agitated fermenter with a height/diameter ratio of around 2.3.

| Agitation: | 300 rpm (two turbine impellers) |
|---|---|
| Aeration: | 300 normal liter air per minute |
| Temperature: | 37° C. |
| Time: | around 59 hours |

Around 59 hours after inoculation 150 liters was transferred from the seed fermenter to the main fermenter. A substrate with the following composition was prepared in a 2500 liter main fermenter:

| Toasted soy meal | 120 kg |
|---|---|
| Maltose | 30 kg |
| Cellulose powder (Arbocel CB-200) | 50 kg |
| Pluronic ® antifoam agent | 200 ml |

Tap water was added to a total volume of around 1200 liters. The toasted soy meal was suspended in water. The pH was adjusted to 6.2 before the substrate was sterilized in the main fermenter for 1½ hours at 123° C.. The final volume before inoculation was around 1550 liters.

Then 150 liters of seed culture was added,

Fermentation conditions were:

Fermenter type: Conventional aerated and agitated fermenter with a height/diameter ratio of around 2.7.

| Agitation: | 250 rpm (two turbine impellers) |
|---|---|
| Aeration: | 1200 normal liter air per minute |
| Temperature: | 37° C. |
| Time: | around 120 hours |

From 24 fermentation hours to around 130 fermentation hours water was added aseptically to the main fermenter at a constant rate of around 4 liters per hour.

Figure 18:
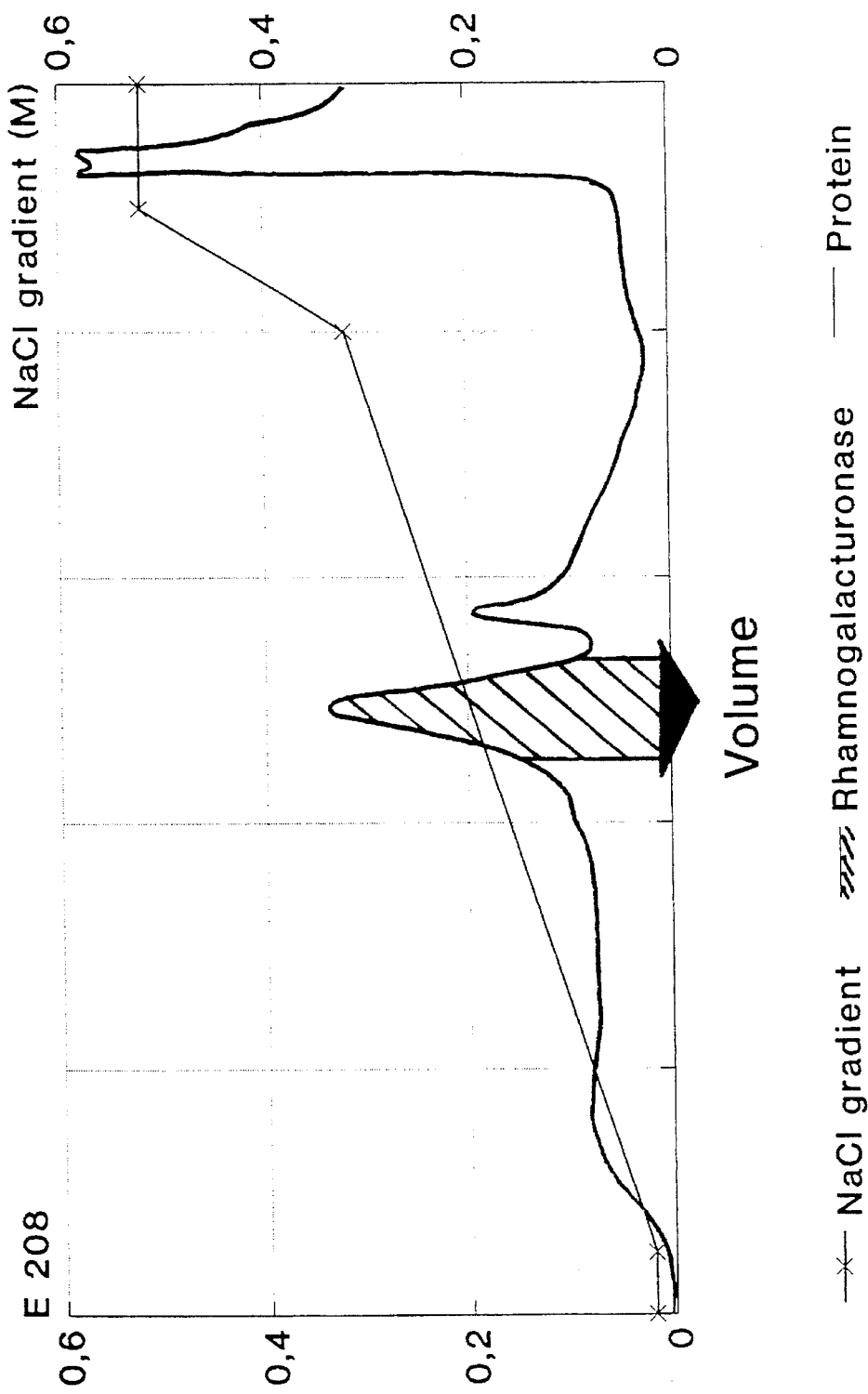
FIG. 18 shows an ion exchange chromatogram of the process for purifying an *Irpex lacteus* rhamnogalacturonase.

The RGase was isolated from the above indicated *Irpex lacteus* enzyme preparation broth in the manner described in Table 3 (FIGS. 16–18).

TABLE 3

*IRPEX LACTEUS:*
RHAMNOGALACTURONASE PURIFICATION

*Irpex lacteus* enzyme broth
|
|
1: ULTRAFILTRATION - DIALYSIS
Filtron Minisette, filter area 3500 cm$^2$,
membrane NMWL 10,000
distilled water; 5 × volume
|
|
2: SAMPLE PREPARATION
addition of solid (NH$_4$)$_2$SO$_4$ to 2M concentration,
pH adjustment to pH 5.0
|
|
3: HIC: PHENYL TOYOPEARL 650 (M), FIG. 16
(column: 5.0 × 26.5 cm, flow 60 ml/min)
eluent: water, decreasing (NH$_4$)$_2$SO$_4$-gradient
2M-concave decrease
(=linear decrease of conductivity)-0.5M-step-0.0M
|
|
4: ULTRAFILTRATION - DIALYSIS
Filtron Minisette, filter area 3500 cm$^2$,
membrane NMWL 10,000
20 mM TRIS-buffer, pH 8.0; 5 × volume
|

TABLE 3-continued

```
                                 |
        5: IEC: WATER ACCELL QMA-PLUS, FIG. 17
           (column: 26.0 × 23.0 cm, flow 16 ml/min)
           eluent = 20 mM TRIS, pH 8.0, increasing NaCl-gradient:
              0.0M-step-0.05M-step-0.1M-step-0.25M-step-0.5M
                                 |
                                 |
              6: ULTRAFILTRATION - DIALYSIS
              Filtron Minisette, filter area 700 cm²,
                  membrane NMWL 10,000
              20 mM NaCl/HCl, pH 3.6; 5 × volume
                                 |
                                 |
         7:IEC: FRACTOGEL EMD SO₃-650 (M), FIG. 18
           (column: 2.6 × 8.4 cm, flow 15 ml/min)
           eluent: 20 mM NaCl/HCl, pH 3.6; increasing NaCl-gradient:
                  0.02M-linear-0.32M-linear-0.52M
                                 |
                                 |
                  RHAMNOGALACTURONASE
``` ad 1:
Liquid exchange in order to prepare for step 2, removal of small particles and about 50% of the colour, dilution to max. 15 mg protein/ml (otherwise the sample will not bind to the column in step 2).
ad 2:
Liquid adaption in order to prepare for step 3.
ad 3:
HIC is hydrophobic interaction chromatography. The rhamnogalacturonase fraction was pooled from 1.07 m to 1.16M $(NH_4)_2SO_4$.
ad 4:
Buffer exchange in order to prepare for step 5.
ad 5:
IEC is ion exchange chromatography. The rhamnogalacturonase fraction that did not bind to the column was pooled and used for step 6.
ad 6:
Buffer exchange in order to prepare for step 7.
ad 7:
IEC is ion exchange chromatography. The rhamnogalacturonase fraction was pooled from 0.18M to 0.22M NaCl.

Now a part of the amino acid sequences is determined:

```
1            5           10         (SEQ ID NO: 14)
Asn—Val—Asn—Leu—Phe—Ile—Thr—Asp—Gly—Ala—Arg 1            5                      (SEQ ID NO: 15)
Ala—Pro—Asp—Gly—Pro—Ala—
```

The *Irpex lacteus* RGase was further characterized, as follows.

Figure 19:
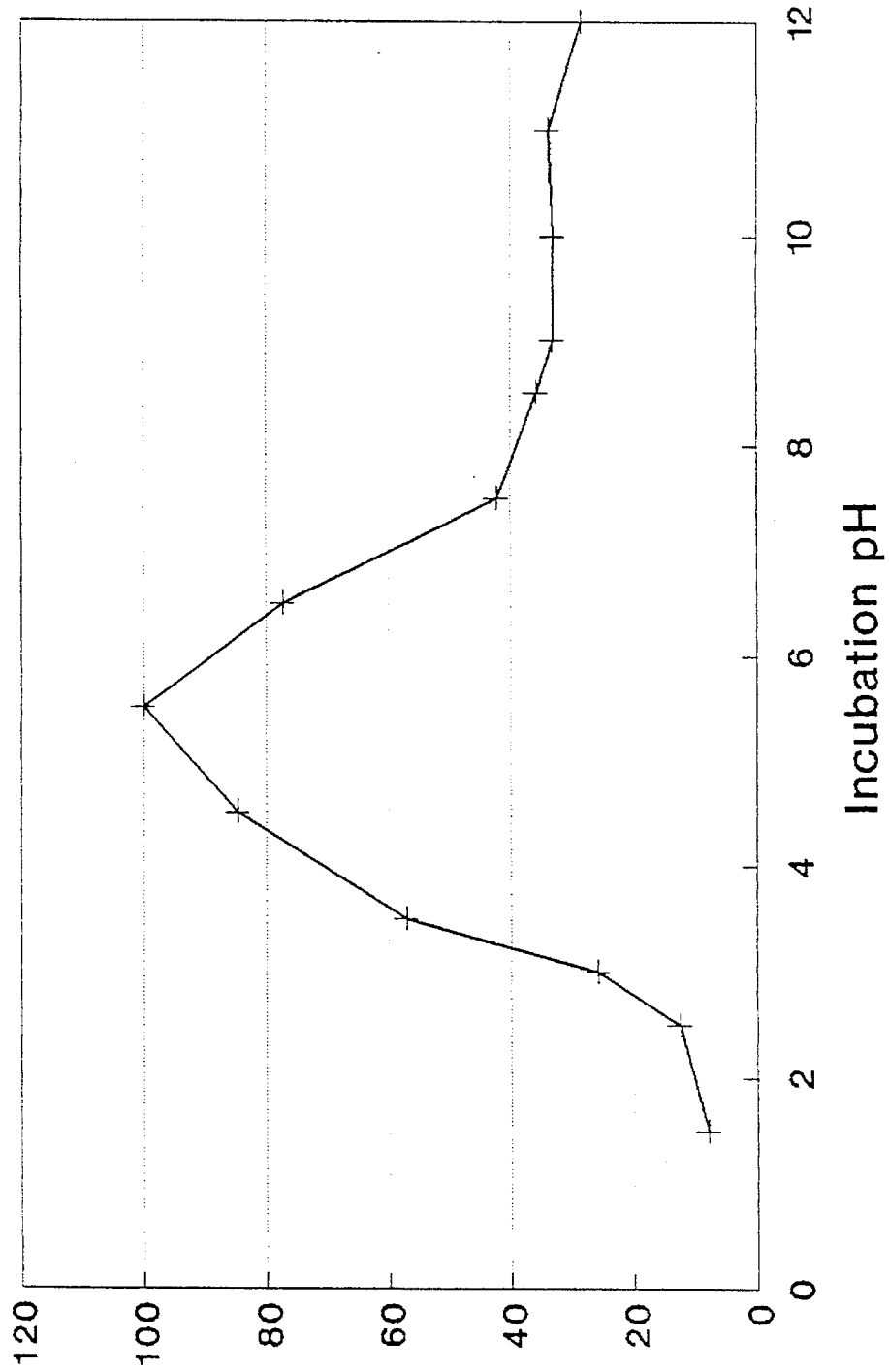
FIG. 19 shows the pH activity of an *Irpex lacteus* rhamnogalacturonase.
Figure 20:
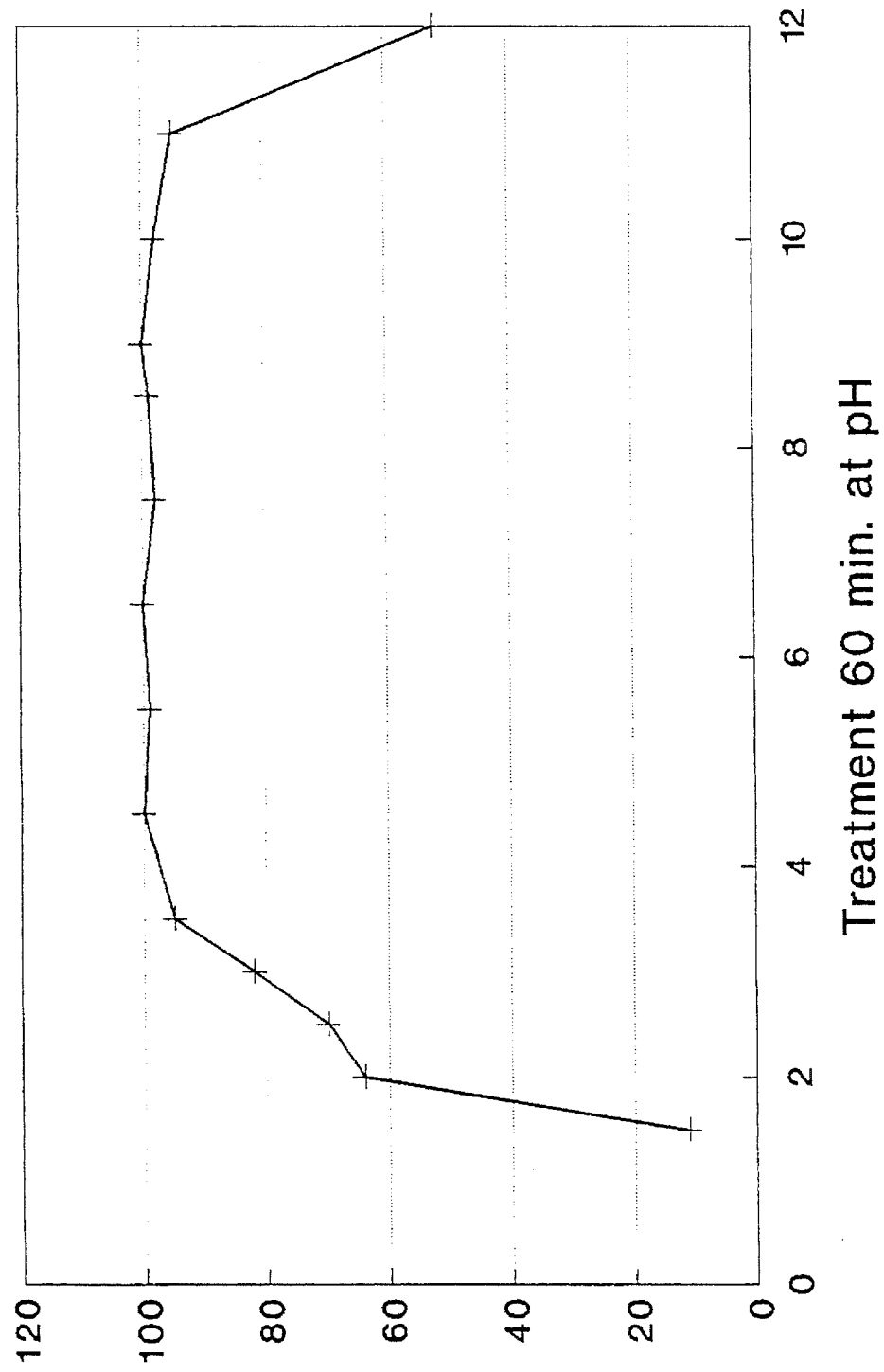
FIG. 20 shows the pH stability of an *Irpex lacteus* rhamnogalacturonase.

FIGS. 19 and 20 show the pH activity and pH stability, respectively.

The pH-optimum is around pH 5.5.

The stability is good between pH 3 and 11 (residual activity ≧80%), when treated for 1 hour at room temperature. Remarkable is the activity in the neutral and alkaline pH-range: At pH 7 still more than 50% of the activity is found, and at pH 8–12 still around 30–35% activity is found. Furthermore, the excellent pH-stability has to be mentioned, a residual activity ≧80% being found at pH 3–12.

Figure 21:
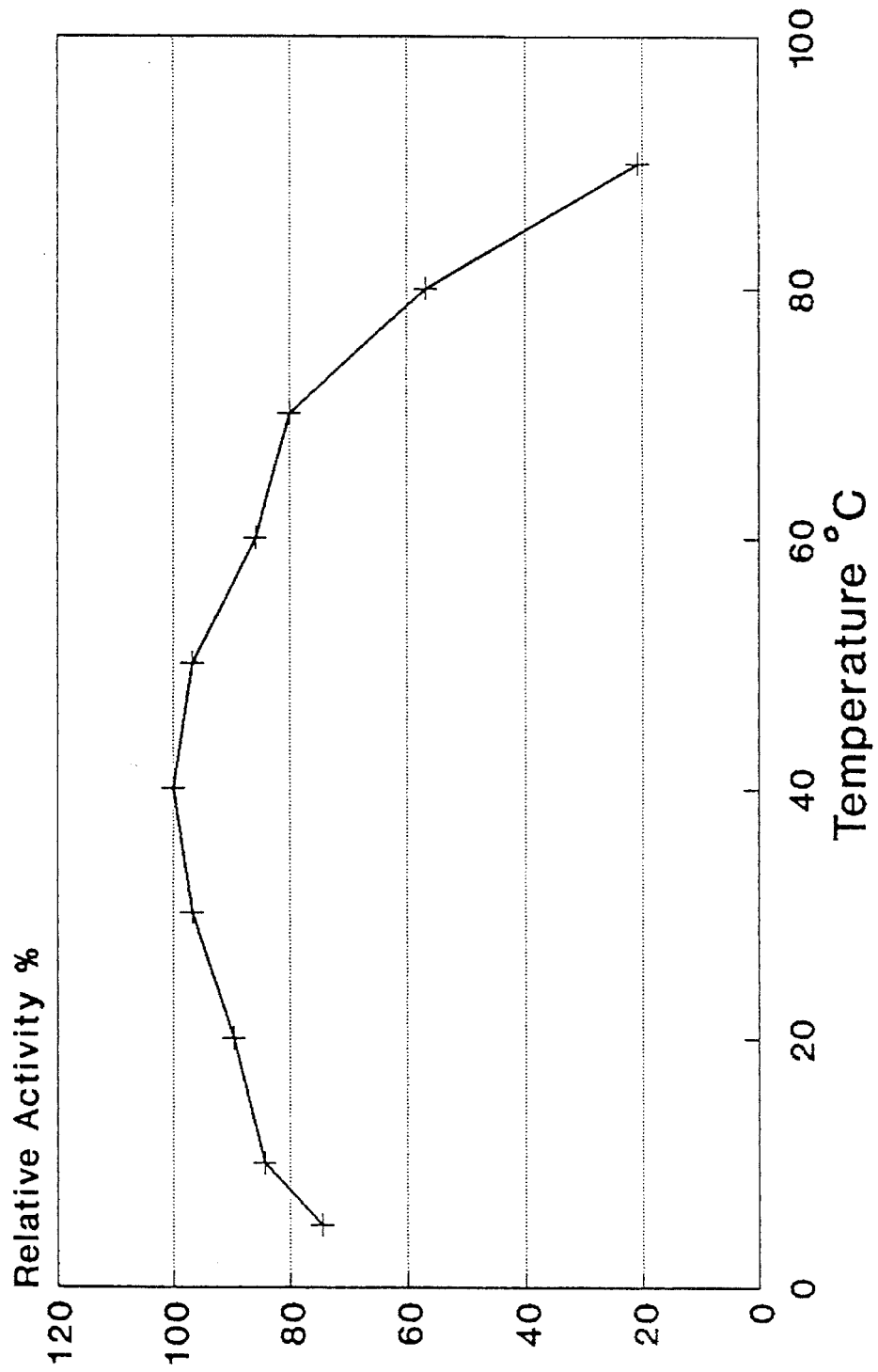
FIG. 21 shows the temperature activity of an *Irpex lacteus* rhamnogalacturonase.
Figure 22:
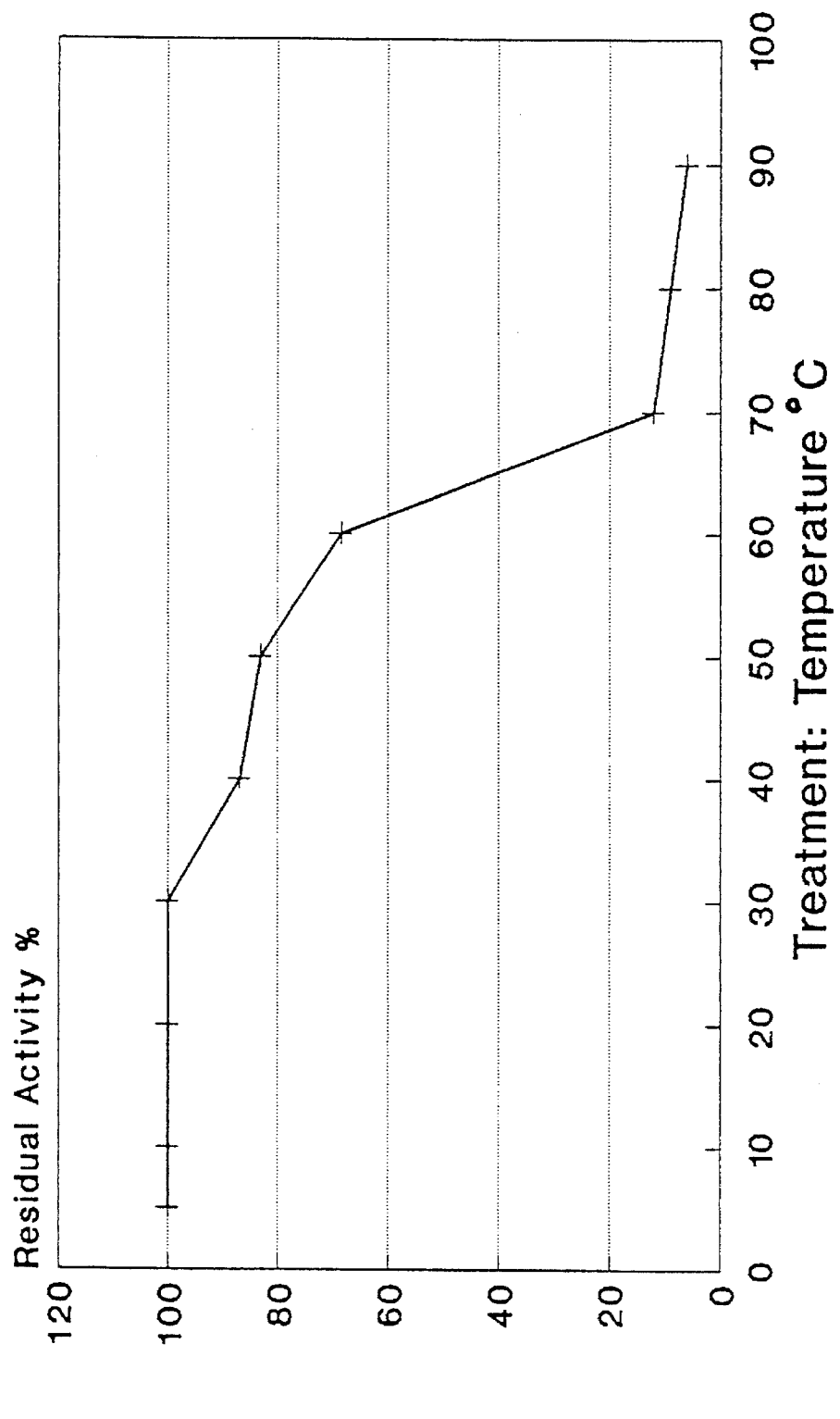
FIG. 22 shows the temperature stability of an *Irpex lacteus* rhamnogalacturonase.

FIGS. 21 and 22 show the temperature activity dependency and the temperature stability dependency, respectively.

The temperature optimum is around 40° C., and the temperature activity range is relatively broad: at 10°–17° C. the activity is ≧80% of the maximum activity, and even at 80° C. more than half of the activity is still present.

For the fruit juice and wine industry the activity in the low temperature range is remarkable: Around 80% activity at 10° C., and around 70% activity at 5° C.

In the temperature range of 5° to 50° C. this RGase is not remarkably influenced after a treatment of 1 hour at pH 4.5 (≧80% of the initial activity). Around 70% of the activity is still found at 60° C., whereas the stability decreases rapidly at temperatures of 70° C. and above.

| Molecular weight: | 45,000 Dalton |
|---|---|
| Isoelectric point: | pH 7.2 |

The below table shows some characteristics of the different RGases isolated from the three identified strains.

| Strains | RGases | pI - range | MW - range |
|---|---|---|---|
| *Aspergillus aculeatus* | | | |
| RGases detected | 6 | 4.0–5.3 | 40,000–65,000 |
| RGase isolated | 1 | 4.6 | 61,000 |
| *Aspergillus japonicus* | | | |
| RGases detected | 11 | 4.2–5.3 | 40,000–65,000 |
| RGase isolated | 1 | 5.3 | 53,000 |
| *Irpex lacteus* | | | |
| RGases detected | 10 | 5.0–9.0 | 40,000–70,000 |
| RGase isolated | 1 | 7.2 | 44,000 |

On the basis of the above indicated amino acid sequences sequence probing processes were carried out for the corresponding cDNA. After isolation of the mRNA, the cDNA was synthesized.

Recombinant DNA molecules according to the invention are constructed and identified in the following manner.

Construction of a *A. aculeatus* cDNA library in *E. coli*

Total RNA is extracted from homogenized *A. aculeatus* mycelium, collected at the time for maximum activity of the RGase, using methods as described by Boel et al. (EMBO J., 3: 1097–1102, 1984) and Chirgwin et al. (Biochemistry (Wash), 18:5294–5299, 1979). Poly(A)-containing RNA is obtained by two cycles of affinity chromatography on oligo(dT)-cellulose as described by Aviv and Leder (PNAS, USA 69:1408–1412, 1972). cDNA is synthesized with the use of a cDNA synthesis kit from Invitrogen according to the manufacturer's description.

Identification of *A. aculeatus* RGase specific cDNA recombinants by use of synthetic oligodeoxyribonucleotides A mixture of synthetic oligodeoxyribonucleotides corresponding to a part of the determined amino acid sequence is synthesized on an Applied Biosystems. Inc. DNA synthesizer and purified by polyacylamide gel electrophoresis. Approximately 150.000 *E. coli* recombinants from the *A. aculeatus* cDNA library is transferred to Whatman 540 paper filters. The colonies are lysed and immobilized as described by Gergen et al. (Nucleic Acids Res. 7, 2115–2135, 1979). The filters are hybridized with the $^{32}$P-labelled RGase specific oligo mixture as described by Boel et al. (EMBO J., 3, 1097–1102, 1984). Hybridization and washing of the filters are done at a temperature 10° C. below the calculated Tm, followed by autoradiography for 24 hours with an intensifier screen. Following autoradiography, the filters are washed at increasing temperatures followed by autoradiography for 24 hours with an intensifier screen. Miniprep plasmid DNA is isolated from hybridizing colonies by 5 standard procedures (Birnboim and Doly Nucleic Acids Res. 7, 1513–1523, 1979), and the DNA sequence of the cDNA insert is established by the Sanger dideoxy procedure. The RGase cDNA fragment is excised from the vector by cleavage with HindIII/XbaI (or other appropriate enzymes) and is purified by agarose gel electrophoresis electroeluted and made ready for ligation reactions. The cDNA fragment is ligated to HindIII/XbaI digested pHD414 to generate pHD RGase in which the cDNA is under transcriptional control of the TAKA promotor from *Aspergillus oryzae* and the AMG terminator from *Aspergillus niger*.

Identification of *A. aculeatus* RGase specific cDNA recombinants using immunological screening procedures.

The cDNA library was split in 50 pools each containing approximately 3000 different cDNA clones. DNA was isolated from the pools and transformed into an appropriate yeast strain. Approximately 20.000 yeast clones (10 plates) were obtained from each of the original pools, in order to ensure that all clones were represented in the yeast library. The yeast clones were replica plated onto minimal agar plates containing galactose. Nitrocellulose filters were placed on top of the yeast colonies followed by incubation of the plates for 2 days at 30° C. The nitrocellulose filters were peeled off and incubated with a monospecific antibody raised against the RGase, using standard immunological procedures. Positive clones were purified twice and rescreened using the same antibody preparations. DNA was isolated from the positive yeast clones, and transformed into *E. coli* MC1061 in order to get higher quantities of DNA. DNA was isolated and analyzed by use of restriction enzymes.

The cDNA was excised from the yeast/*E. coli* vector using HindIII/XbaI, purified on gel and inserted into the Aspergillus expression vector pHD414 as described in this specification.

Construction of an Aspergillus expression vector

Figure 23:
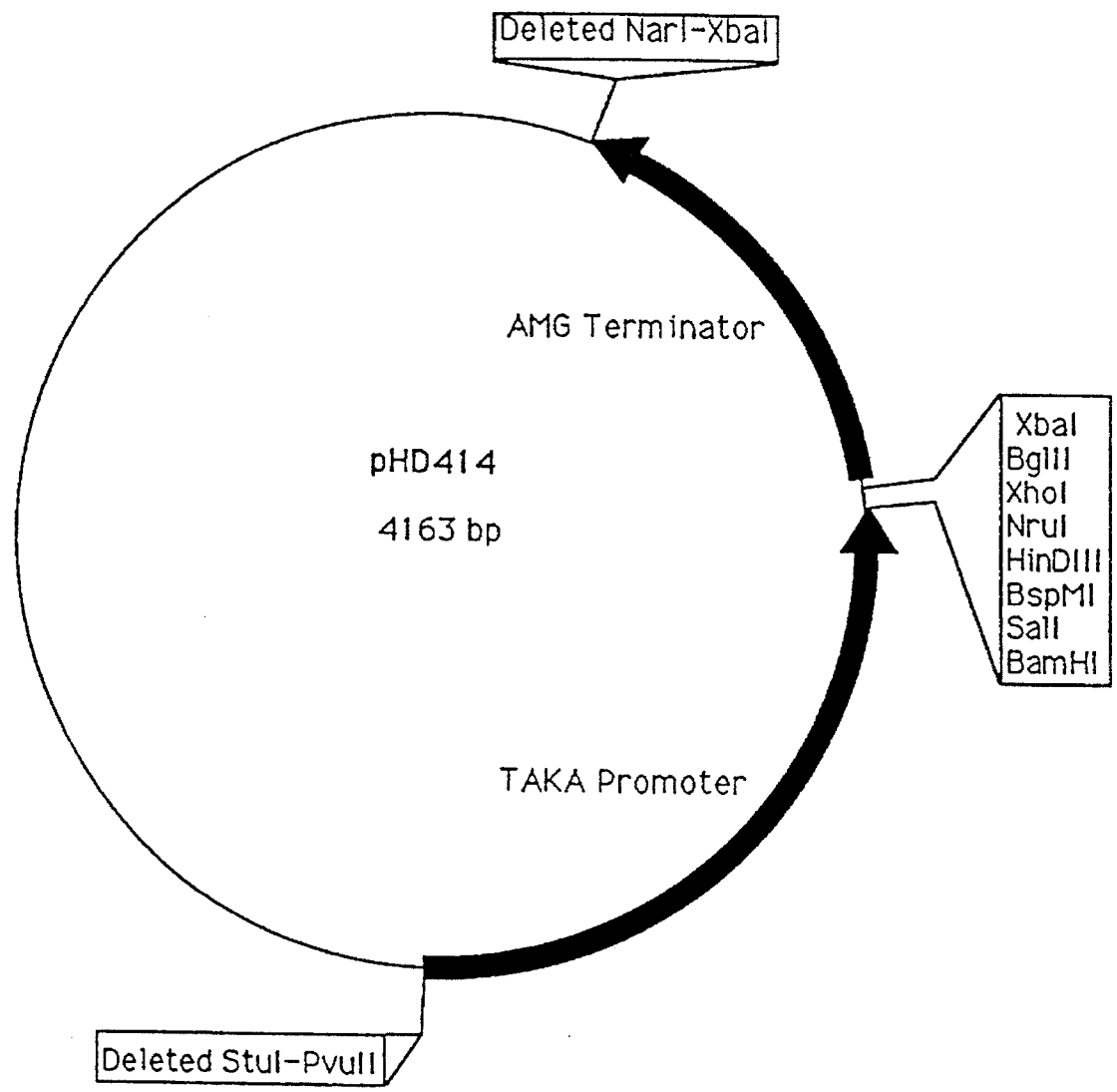
FIG. 23 shows a map of the expression vector pHD414.

The vector pHD414 (FIG. 23) is a derivative of the plasmid p775 (described in EP 238 023). In contrast to this plasmid, pHD414 has a string of unique restriction sites between the promoter and the terminator. The plasmid was constructed by removal of an approximately 200 bp long fragment (containing undesirable RE sites) at the 3 end of the terminator, and subsequent removal of an approximately 250 bp long fragment at the 5' end of the promoter, also containing undesirable sites. The 200 bp region was removed by cleavage with NarI (positioned in the pUC vector) and XbaI (just 3' to the terminator), subsequent filling in the generated ends with Klenow DNA polymerase +dNTP, purification of the vector fragment on gel and religation of the vector fragment. This plasmid was called pHD413. pHD413 was cut with StuI (positioned in the 5'end of the promoter) and PvuII (in the pUC vector), fractionated on gel and religated, resulting in pHD414. FIG. 23 is a map of plasmid pHD414, wherein "AMG Terminator" indicates the *A. niger* glucoamylase terminator, and "TAKA Promoter" indicates the *A. oryzae* TAKA amylase promoter.

Transformation of *Aspergillus oryzae* or *Aspergillus niger* (general procedure)

100 ml of YPD (Sherman et al., Methods in Yeast Genetics, Cold Spring Harbor Laboratory, 1981) is inoculated with spores of *A. oryzae*, *A. niger* or argB mutants hereof and incubated with shaking at 37° C. for about 2 days. The mycelium is harvested by filtration through miracloth and washed with 200 ml of 0.6M $MgSO_4$. The mycelium is suspended in 15 ml of 1.2M $MgSO_4$ 10 mM $NaH_2PO_4$, pH=5.8. The suspension is cooled on ice and 1 ml of buffer containing 120 mg of Novozym® 234, batch 1687 is added.

After 5 minutes 1 ml of 12 mg/ml BSA (Sigma type H25) is added and incubation with gentle agitation continued for 1.5–2.5 hours at 37° C. until a large number of protoplasts is visible in a sample inspected under the microscope.

The suspension is filtered through miracloth, the flitrate transferred to a sterile tube and overlayered with 5 ml of 0.6M sorbitol, 100 mM Tris-HCII, pH=7.0. Centrifugation is performed for 15 minutes at 100 g and the protoplasts are collected from the top of the $MgSO_4$ cushion. 2 volumes of STC (1.2M sorbitol, 10 mM Tris-HCl, pH=7.5. 10 mM $CaCl_2$) are added to the protoplast suspension and the mixture is centrifuged for 5 minutes at 1000 g. The protoplast pellet is resuspended in 3 ml of STC and repelleted. This is repeated. Finally the protoplasts are resuspended in 0.2–1 ml of STC.

100μof protoplast suspension is mixed with 5–25 μg of the appropriate DNA in 10μl of STC. Protoplasts from the argB strains are mixed with pSal43 DNA (an *A. nidulans* argB gene carrying plasmid) and protoplasts from the argB+ strains are mixed with p3SR2 (an *A. nidulans* amdS gene carrying plasmid). The mixture is left at room temperature for 25 minutes. 0.2 ml of 60% PEG 4000 (BDH 29576). 10 mM $CaCl_2$ and 10 mM Tris-HCl, pH=7.5 is added and carefully mixed (twice) and finally 0.85 ml of the same solution is added and carefully mixed. The mixture is left at room temperature for 25 minutes, spun at 2500 g for 15 minutes and the pellet is resuspended in 2 ml of 1.2M sorbitol. After one more sedimentation the protoplasts are spread on the appropriate plates. Protoplasts from the argB strains transformed with pSal 43 are spread on minimal plates (Cove Biochem. Biophys.Acta 113 (1966) 51–56) with glucose and urea as carbon and nitrogen sources, respectively, and containing 1.2M sorbitol for osmotic stabilization. Protoplasts from the argB-strains transformed with p3SR2 are spread on minimal plates (Cove Biochem. Biophys.Acta 113 (1966) 51–56) containing 1.0M sucrose, pH=7.0, 10 mM acetamide as nitrogen source and 20 mM CsCl to inhibit background growth. After incubation for 4–7 days at 37° C. spores are picked, suspended in sterile water and spread for single colonies. This procedure is repeated and spores of a single colony after the second reisolation is stored as a defined transformant.

Production of RGase in high yield with this transformed host:

Expression of recombinant *A. aculeatus* RGase in an *A. oryzae* strain pHD RGase is transformed into *A. oryzae* IFO 4177 by cotransformation with p3SR2 containing the amdS gene from *A. nidulans* as described with a mixture of equal amounts of pHD RGase and p3SR2 (approximately 5μg of each). Transformants which can use acetamide as sole nitrogen source are reisolated twice. After growth on YPD (Sherman et al. 1981) for three days culture supernatants are analysed by SDS-PAGE. The gels are stained with coomassie brilliant blue R. The best transformants are selected for further studies and grown in a 2 liter Kieler fermentor on 4% soy bean meal and supplied with glucose during growth. The culture is heavily agitated during fermentation. The recombinant product is isolated from the culture broth by removal of the cells by centrifugation, ultrafiltration of the supernatant and freeze drying.

Expression of RGase in an *A. niger* strain pHD RGase is transformed into *A. niger* argB by cotransformation with pSal43 containing the argB gene form *A.*

*nidulans* as described earlier. Protoplast are incubated with equal amounts, approximately 5µg of each plasmid. Transformants are selected on minimal plates (Cove Biochem. Biophys.Acta 113 (1966), 55–56) by relief of argenine requirement.

After two reisolations of conidiospores the transformants are cultured for seven days in YPD (Sherman et al., 1981) at 30° C. The culture supernatants are analyzed by SDS-PAGE. Most of the transformants produced RGase in their supernatants.

Production of RGase using a transformed host other than Aspergillus species without significant amounts of accompanying similar enzymes.

Expression of RGase in *S. cerevisiae*

The RGase gene is isolated from pHD RGase and introduced into the yeast expression vector pYHD5 in which the cDNA is under transcriptional control of the Gal 1–10 promoter and the α-factor terminator. A URA3 mutant yeast strain is. transformed with the yeast expression plasmid by the Li/salt procedure. Transformants are selected on minimal agar plates without uracil. The transformants are replica plated to minimal agar plate without uracil, but supplemented with galactose (in order to induce the promoter) and tested for expression of RGase by use of antibodies and by measurement of the enzyme activity.

Expression of RGase in *E. coli*

The RGase cDNA is excised from pHD RGase using HindIII/XbaI. The fragment is treated with Klenow DNA polymerase and dNTP in order to make blunt ended DNA molecules and purified on gel. The fragment is cloned into the vector pHD282 in the PvuII site (Dalboege et al., Gene, 79, 325–332, 1989). and in a subsequent mutation step using standard site directed mutagenesis techniques, fused directly in frame to the OmpA signal peptide in pHD282.

The OmpA-RGase chimeric gene is transferred to the expression vector pHD 234 as a ClaI/BamHI fragment and transferred into *E. coli* MC1061 (Casadaban and Cohen, J. Mal.Biol., 138, 179–207, 1980) to generate recombinant clones. *E. coli* MC1061 containing the expression plasmid is grown in 1.5 liter MBR reactor equipped with temperature, pH, air-flow rate and agitation controllers. The medium contained 40 mg tryptone/ml (Difco) and 20 mg yeast extract/ml. Production of RGase is induced by raising the temperature from 28° C. to above 37° C. at an $A_{525}=50$.

The bacteria samples are analyzed by SDS-PAGE and activity measurements.

The RGase according to the invention can be used as a plant cell wall degrading enzyme, thus including the applications shown on page 35 of GB 2115820A.

If the RGase according to the invention is used together with Pectinex Ultra SP and/or an acetyl esterase, a synergistic effect can be demonstrated.

EXAMPLE 1

Pectin extraction

Pectins have gelation and stabilisation properties, which make them useful for the food industry. They are commercially extracted from waste materials of the food industry, e.g. citrus peels, apple pomace or sugar-beet pulp.

Most often the extraction with acids (sulphuric acid or nitric acid) is used for the production of pectins. At a pH around 2 and at an elevated temperature the pectins are extracted from plant material and precipitated with alcohol after precipitation.

This acid extraction has several disadvantages: water pollution, corrosion, filtering problems due to disintegration of the plant cell walls, partial break down of the wanted pectin polymers (the degree of polymerisation is one of the most important parameters of a commercial pectin). Thus, it is obvious, that an extraction of pectins with enzymes, which do not decompose native pectin polymers would be of great advantage.

Industrial apple pormace for the pectin production was used to compare the amount of pectin extractable either by chemicals or RGases.

Chemical extraction of pectin (prior art)

To 1 part of pormace 19 parts of distilled water was added and the mixture was heated to the boiling point in order to bring the soluble part of the pomace into solution. The pH value was adjusted to 1.9 by means of 2N $H_2SO_4$. The mixture is held at this pH for 2.5 hours at 90° C. and afterwards cooled to room temperature. The mixture is filtered and the pomace residues washed with 10 parts of distilled water.

To 1 part of the flitrate 6 parts of methanol is added. After 30 minutes standing the mixture is filtered and pressed. The alcohol insoluble substance (AIS) is washed with 4 parts of methanol and filtered and pressed again.

The obtained AIS is dried at 60° C. for one hours.

From this AIS the amount of starch is determined with the test kit from Boehringer Mannheim (order no. 207748).

The amount of obtained pectin is calculated by determination of the amount of AIS in % obtained from the dry matter substance from the pomace and subtracting the amount of starch in the AIS.

Enzymatic extraction of pectin

To 1 part of pomace 19 parts of 0.1m sodium acetate buffer of pH 5.0 (with 0.02% $NAN_3$) is added. At 30° C. the mixture is treated for 20 hours with solutions of the purified RGases according to the invention originating from *A. aculeatus* and *A. japonicus*. Afterwards the mixture is filtered and the pomace residues washed with 10 parts of distilled water.

The AIS is obtained in the way described above.

Results

With the chemical extraction 17.5% pectin was obtained whereas with the enzymatic extraction between 9 and 11% were obtained, depending upon the type and amount of RGase used.

These results prove, that the RGase is one of the key enzymes for enzymatic extraction of pectins from plant material. Also, it appears from the above that 50 to 60% of the pectin extractable by chemical means and with all the accompanying disadvantages can be extracted enzymatically in an environmental sound manner, especially when this enzyme will be combined with other pectin liberating activities, e.g. β1,4-galactanase. This ability of extracting pectins from the plant cell wall proves that RGase is important for the production of cloudy juices, nectars and purees (stabilization of the cloud and the desired consistency of a product).

EXAMPLE 2

Citrofiber DF50 (from Citrosuco Paulisto S/A, Matao, Brazil) is a commercially available dietary fiber product, derived from orange juice pulp. It is a by-product from citrus juice processing containing the juice vesicle membranes and segment walls from oranges. This product consists of cellulolytic and non-cellulolytic polysaccharides such as pectins and hemicelluloses.

A liquefaction of this citrofiber in order to change the soluble/insoluble solids ratio of this fiber will result in a better application value and offers new possibilities for formulating this fibers in other products: e.g. juices, soft drinks, and liquid health products.

Figure 24:
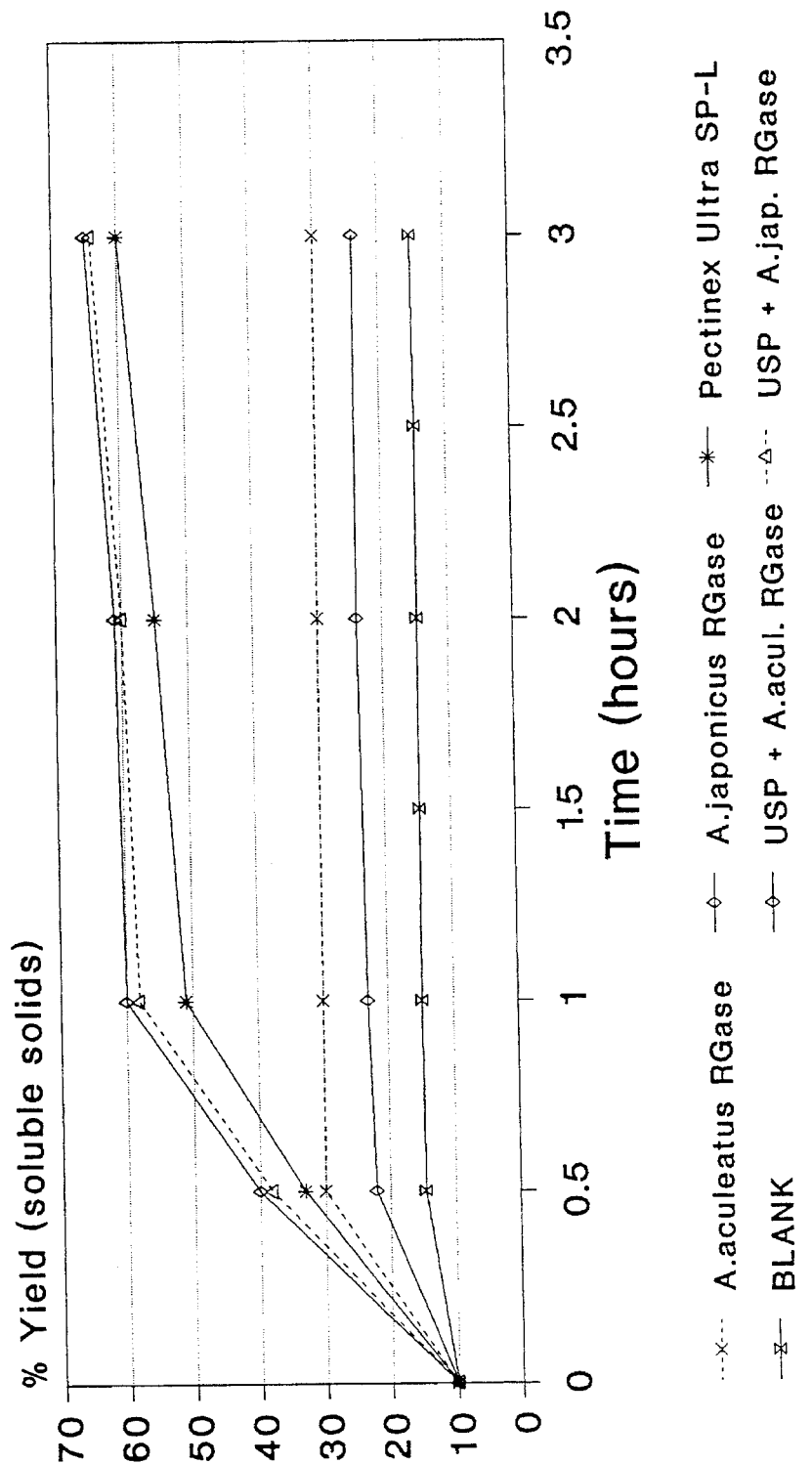
FIG. 24 shows the effect of rhamnogalacturonases on liquefaction.

FIG. 24 shows that RGase is one of the key activities for the liquefaction of this citrofiber. RGase alone can increase the soluble part from around 15% to 25–30% in respect to the RGase used.

The functionality of Pectinex® Ultra SP-L, a multi-enzyme complex for liquefaction containing RGase (*Aspergillus aculeatus*) in certain amounts, could even be improved by boosting the RGase activity. By doubling of the amount of RGase in Pectinex® Ultra SP-L an increase of 5–10% of the soluble solids (in respect to treatment time) was obtained.

Besides the higher degree of liquefaction a shortening of the processing time is possible. This again proves the importance of RGase for liquefaction of plant cell walls.

We claim:

1. An isolated rhamnogalacturonase derived from a strain of *Aspergillus japonicus* which:
   (a) has a pH-optimum between 6.5 and 7.0;
   (b) retains at least 80% of the maximal activity throughout the pH range of 5.5–12;
   (c) has a temperature optimum of about 40° C.; and
   (d) retains at least 80% of the maximal activity throughout the temperature range of 20°–60° C.

2. A rhamnogalacturonase according to claim 1 which has an isoelectric point of 2.5–3.5.

3. A rhamnogalacturonase according to claim 1 which has a molecular weight between 30,000 and 50,000.

4. A rhamnogalacturonase according to claim 1, wherein the strain is ATCC 20236.

5. A rhamnogalacturonase according to claim 1 which has an N-terminal sequence:

Ala—Phe—Gly—Ile—Thr—Thr—Ser—Ser—Ser—Ala—Tyr—Val—Ile—Asp—Thr— (SEQ ID NO: 13)
1               5                       10                      15
Asp—Ala—Pro—Asn—Gln—Leu—Lys—Xaa—Thr—Val—Ser—Arg.
                20                      25

6. An enzyme preparation comprising a rhamnogalacturonase according to claim 1 and a plant cell wall degradation or modification agent.

7. The enzyme preparation according to claim 6, wherein the plant cell wall degradation or modification agent is a pectinase, cellulase or hemicellulase.

8. A DNA sequence which codes for a rhamnogalacturonase according to claim 1.

9. A method of degrading or modifying plant cell walls, comprising adding a rhamnogalacturonase according to claim 1 to said plant cell walls or components thereof.

10. A method of degrading or modifying plant cell walls, comprising adding an enzyme preparation according to claim 1 to said plant cell walls or components thereof.

11. An isolated rhamnogalacturonase derived from a strain of *Aspergillus aculeatus* which:
    (a) has a pH-optimum of about 5.0;
    (b) retains at least 80% of the maximal activity throughout the pH range of 3–6.5;
    (c) has a temperature optimum of about 40° C.; and
    (d) retains at least 80% of the maximal activity throughout the temperature range of 5°–50° C.

12. The rhamnogalacturonase according to claim 11, wherein the strain is CBS 101.43.

13. The rhamnogalacturonase according to claim 11 which has the following partial amino acid sequences:

Gly—Ala—Val—Gln—Gly—Phe—Gly—Tyr—Val—Tyr—His—Ala—Glu—Gly—Thr (SEQ ID NO: 1)
1               5                       10                      15
Tyr—Gly—Ala—Arg

Ser—Xaa—Asn—Ile—Leu—Ser—Tyr—Gly—Ala—Val—Ala—Asp—Xaa—Ser—Thr— (SEQ ID NO: 2)
1               5                       10                      15
Asp—Val—Gly—Pro—Ala—Ile—Thr—Ser—Ala—Xaa—Ala—Ala—Arg—Lys
                20                      25

Ser—Arg—Asn—Ile (SEQ ID NO: 3)
1

Ser—Ala—Tyr—Gly—Ser—Gly—Tyr—Xaa—Leu—Lys (SEQ ID NO: 4)
1               5                       10

Thr—Leu—Glu—Asp—Ile—Ala—Ile (SEQ ID NO: 5)
1               5

Gly—Leu—Xaa—Ala—Xaa—Ile—Pro—Ile—Pro—Xaa—Ile—Pro—Pro—Xaa—Phe— (SEQ ID NO: 6)
1               5                       10                      15
Phe

Ser—Leu—Asp—Ile—Asp—Gly—Tyr (SEQ ID NO: 7)
1               5

Ser—Val—His—Asp—Ile—Ile—Leu—Val—Asp—Ala—Pro—Ala—Phe (SEQ ID NO: 8)
1               5                       10

Ala—Ala—Asp—Leu—Ala— (SEQ ID NO: 9)
1               5

Gly—Ser—Asn—Ile (SEQ ID NO: 10)
1

Tyr—Pro—Gly—Leu—Thr—Pro—Tyr (SEQ ID NO: 11)
1               5 and

Asn—Val—Tyr—Thr—Trp—Ser—Ser—Asn—Gln—Met—Tyr—Met—Ile—Lys. (SEQ ID NO: 12)
1               5                       10

14. An isolated rhamnogalacturonase derived from a strain of *Irpex lacteus* which (a) has a pH-optimum of about 5.5;

(b) retains at least 80% of the maximal activity throughout the pH range of 3–12;

(c) has a temperature optimum of about 40° C.; and (d) retains at least 80% of the maximal activity throughout the temperature range of 10°–17° C.

15. The rhamnogalacturonase according to claim 14, wherein the strain is ATCC 20157.

16. The rhamnogalacturonase according to claim 14 which has the following partial amino acid sequences:

(SEQ ID NO: 14)

Asn—Val—Asn—Leu—Phe—Ile—Thr—Asp—Gly—Ala—Arg
1　　　　　　　　5　　　　　　　　　　10 and

Ala—Pro—Asp—Gly—Pro—Ala—.　　　(SEQ ID NO: 15)
1　　　　　　　　5

* * * * *